(12) United States Patent
Edwards et al.

(10) Patent No.: US 6,670,398 B2
(45) Date of Patent: Dec. 30, 2003

(54) COMPOUNDS AND METHODS FOR TREATING TRANSPLANT REJECTION

(75) Inventors: David B. Edwards, Alpharetta, GA (US); Patricia K. Somers, Fort Collins, CO (US); Mitchell Glass, Atlanta, GA (US)

(73) Assignee: AtheroGenics, Inc., Alpharetta, GA (US)

(*) Notice: Subject to any disclaimer, the term of this patent is extended or adjusted under 35 U.S.C. 154(b) by 200 days.

(21) Appl. No.: 10/036,307

(22) Filed: Oct. 25, 2001

(65) Prior Publication Data

US 2002/0156022 A1 Oct. 24, 2002

Related U.S. Application Data

(63) Continuation-in-part of application No. 09/370,046, filed on Aug. 6, 1999, now Pat. No. 6,548,699, which is a continuation of application No. 09/079,213, filed on May 14, 1998, now Pat. No. 6,147,250, and a continuation-in-part of application No. 09/815,262, filed on Mar. 21, 2001.

(60) Provisional application No. 60/047,020, filed on May 14, 1997, and provisional application No. 60/191,046, filed on Mar. 21, 2000.

(51) Int. Cl.$^7$ ............................................. C07C 321/00
(52) U.S. Cl. ........................ 514/571; 514/543; 562/426
(58) Field of Search ........................ 562/426; 514/543, 514/571

(56) References Cited

U.S. PATENT DOCUMENTS

| | | |
|---|---|---|
| 3,179,701 A | 4/1965 | Rocklin |
| 4,029,812 A | 6/1977 | Wagner et al. |
| 4,076,841 A | 2/1978 | Wagner et al. |
| 4,078,084 A | 3/1978 | Wagner et al. |
| 4,115,590 A | 9/1978 | Lerner |
| 4,752,616 A | 6/1988 | Hall et al. |
| 4,755,524 A | 7/1988 | Mueller et al. |
| 4,954,514 A | 9/1990 | Kita et al. |
| 4,968,710 A | 11/1990 | Rustad |
| 4,975,467 A | 12/1990 | Ku et al. |
| 5,043,330 A | 8/1991 | Nguyen et al. |
| 5,061,734 A | 10/1991 | Mao et al. |
| 5,066,822 A | 11/1991 | Rustad |
| 5,084,214 A | 1/1992 | Kita et al. |
| 5,112,870 A | 5/1992 | Mao et al. |
| 5,206,247 A | 4/1993 | Regnier et al. |
| 5,262,439 A | 11/1993 | Parthasarathy |
| 5,294,724 A | 3/1994 | Jendralla et al. |
| 5,310,949 A | 5/1994 | Dufresne et al. |
| 5,411,741 A | 5/1995 | Zaias |
| 5,426,196 A | 6/1995 | Fang |
| 5,608,095 A | 3/1997 | Parker et al. |
| 5,627,205 A | 5/1997 | Regnier et al. |
| 5,693,337 A | 12/1997 | Suzuki et al. |
| 5,739,374 A | 4/1998 | Janssen et al. |
| 5,770,355 A | 6/1998 | Brocia |
| 6,037,377 A | 3/2000 | Anderskewitz et al. |
| 6,121,319 A | 9/2000 | Somers |
| 6,147,250 A | 11/2000 | Somers |
| 6,323,359 B1 | 11/2001 | Jass |
| 6,448,019 B1 | 9/2002 | Mendelsohn et al. |

FOREIGN PATENT DOCUMENTS

| | | |
|---|---|---|
| DE | 27 16 125 A 1 | 10/1977 |
| EP | 0 190 682 A2 | 8/1986 |
| EP | 0 212 310 A2 | 3/1987 |
| EP | 0 254 272 A2 | 1/1988 |
| EP | 0 292 660 A2 | 11/1988 |
| EP | 0 317 165 A1 | 5/1989 |
| EP | 0 348 203 A1 | 12/1989 |
| EP | 0 405 788 A2 | 1/1991 |
| EP | 0 621 255 A1 | 10/1994 |
| EP | 418648 B1 | 11/1995 |
| EP | 0 763 527 A1 | 3/1997 |
| EP | 0 866 049 A2 | 9/1998 |
| FR | 2.130.975 | 11/1972 |
| FR | 2.133.024 | 11/1972 |
| FR | 2.134.810 | 12/1972 |
| FR | 2.140.769 | 1/1973 |
| FR | 2.168.137 | 8/1973 |
| GB | 1136539 | 12/1968 |
| GB | 1148550 | 4/1969 |
| GB | 1199871 | 7/1970 |
| JP | 73-28425 | 12/1995 |
| WO | 93/02051 | 2/1993 |
| WO | 94/07869 | 4/1994 |
| WO | 95/09158 | 4/1995 |
| WO | 95/15760 | 6/1995 |
| WO | 95/17408 | 6/1995 |
| WO | 95/30415 | 11/1995 |

(List continued on next page.)

OTHER PUBLICATIONS

Meng et al.; "Novel Phenolic Antioxidants as Multifunctional Inhibitors of Inducible VCAM–1 Expression for Use in Atherosclerosis," *Bioorganic & Medicinal Chemistry Letters*; (2002); pp. 2545–2548.

(List continued on next page.)

*Primary Examiner*—Paul J. Killos
(74) *Attorney, Agent, or Firm*—Sherry M. Knowles, Esq.; King & Spalding LLP; Alan L. Scrivner, Esq.

(57) ABSTRACT

The use of compounds of the formula

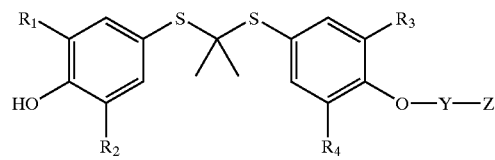

and pharmaceutically acceptable salts thereof, alone or in combination for the treatment of transplant rejection, wherein the substituents are further defined in the application.

25 Claims, 3 Drawing Sheets

FOREIGN PATENT DOCUMENTS

| WO | 96/12703 | 5/1996 |
| --- | --- | --- |
| WO | 97/15546 | 5/1997 |
| WO | 97/26258 | 7/1997 |
| WO | 97/48694 | 12/1997 |
| WO | 98/22418 | 5/1998 |
| WO | 98/30255 | 7/1998 |
| WO | 98/42327 | 10/1998 |
| WO | Wo 98/51289 A2 | 11/1998 |
| WO | 99/15159 | 4/1999 |
| WO | 99/24400 | 5/1999 |
| WO | 00/26167 | 5/2000 |
| WO | 00/26184 | 5/2000 |
| WO | 00/31053 | 6/2000 |
| WO | 00/53795 | 9/2000 |
| WO | 00/59509 | 10/2000 |

OTHER PUBLICATIONS

Rinninger et al.; "Probucol Enhances Selective Uptake of HDL–Associated Cholesteryl Esters In Vitro by a Scavenger Receptor B–I–Dependent Mechanism," *Artherioscler Thromb Vasc Biol.*; (1999); vol. 19; pp. 1325–1332.

Sawayama, et al.; "Effects of Probucol and Pravastatin on Common Carotid Atherosclerosis in Patients with Asymptomatic Hypercholesterolemia," *Journal of the American College of Cardiology*; Vol 39; No. 4; (2002); pp. 610–616.

Barnhart, J.W., et al., The Synthesis, Metabolism, and Biological Activity of Probucol and its Analogs, *Pharmacochem. Libr. No. 17*, (1991), pp. 277–299.

BioCentury Extra (The Bernstein Report of BioBusiness), "AtheroGenics: Faster than Anticipated," (Reprint from May 29, 2001).

Chemical Abstracts Service, Columbus, Ohio, US; STN, *Chemical Abstracts*, 28–Heterocyclic Compounds (More Than One Hetero Atom), vol. 124, No. 1, 1996, p. 921.

Chemical Abstracts Service, Columbus, Ohio, US; STN, *Chemical Abstracts*, 28–Heterocyclic Compounds (More Than One Hetero Atom), vol. 124, No. 11, 1996, p. 1251.

Cominacini et al., Antioxidants Inhibit the Expression of Intercellular Cell Adhesion Molecule–1 and Vascular Cell Adhesion Molecule–1 Induced by Oxidized LDL on Human Umbilical Vein Endothelial Cells, *Free Radical Biology & Medicine*, vol. 22, No. 1/2, pp. 117–127, 1997.

DeMeglio, P. et al., Farmaco, Ed. Sci., 40(11), 833–844 (1985) (partial English language translation).

Feldman et al., The in vitro and ex vivo antioxidant properties, and hypolipidemic activity of CGP 2881, *Atherosclerosis*, vol. 144, No. 2 (Jun. 1999), pp. 343–355.

Press Release, Nov. 12, 2001, "AtheroGenics Announces Positive Phase II Results From CART–1 Clinical Trial for Restenosis".

Fruebis et al., A Comparison of the Antiatherogenic Effects of Probucol and of a Structural Analogue of Probucol in Low Density Lipoprotein Receptor–deficient Rabbits, *J. Clin. Invest.*, vol. 94, Jul. 1994, pp. 392–398.

Gershbein et al., Ation of Drugs and Chemical Agents on Rat Liver Regeneration, *Drug and Cheical Toxicology*, 8(3), 125–143 (1985).

Chemical Abstracts Service, Columbus, Ohio, US; STN, accession No. 122:187387J, see abstract, Kobayashi et al., vol. 122, 1995.

Chemical Abstracts Service, Columbus, Ohio, US; STN, accession No. 94:30290c, see abstract, Mamedov et al., vol. 94, 1981.

Mao et al., Attenuation of Atherosclerosis in a Modified Strain of Hypercholesterolemic Watanabe Rabbits With Use of a Probucol Analogue (MDL 29,311) That Does Not Lower Serum Cholesterol, *Arteriosclerosis and Thrombosis*, vol. 11, No. 4, Jul./Aug. 1991.

Mao et al., Antioxidant Acitivty of Probucol and Its Analogues in Hypercholesterolemic Watanabe Rabbits, *Journal of Medicinal Chemistry*, 1991, vol. 34, pp. 298–302.

Chemical Abstracts Service, Columbus, Ohio, US; STN, accession No. 86:5066m, see abstract; Medvedev et al., vol. 86, 1997, p. 437.

Chemical Abstracts Service, Columbus, Ohio, US; STN, accession No. 1970:445047, XP002124423; see abstract; Neuworth et al., *J. Med. Chem.*, (1970), vol. 13, No. 4, 722–725.

Chemical Abstracts Service, Columbus, Ohio, US; STN, accession No. 110:212254a, see abstract; Pastor et al., vol. 110, 1989.

Ramasamy et al., Modulation of Expression of Endothelial Nitric Oxide Synthase by Nordihydroguaiaretic Acid, a Phenolic Antioxidant in Cultured Endothelial Cells, *Modlecular Pharmacology*, vol. 56, No. 1, Jul. 1999, pp. 116–123.

Roberts et al., Regulation of monocyte to macrophage differentiation by antiglucocorticoids and antioxidants, *American Journal of Obstetrics and Gynecology*, vol. 179, No. 2, Aug. 1998, pp. 354–362.

Chemical Abstracts Service, Columbus, Ohio, US; STN, see abstract; Tomich et al., vol. 127, No. 6, 1997.

Chemical Abstracts Service, Columbus, Ohio, US; STN, accession No. 126:277465v, see abstract; Toshiaki et al., vol. 126, No. 21, 1997, p. 669.

Chemical Abstracts Service, Columbus, Ohio, US; STN, accession No. 86189w, see abstract; Wagner, Jr., et al., vol. 82, 1975.

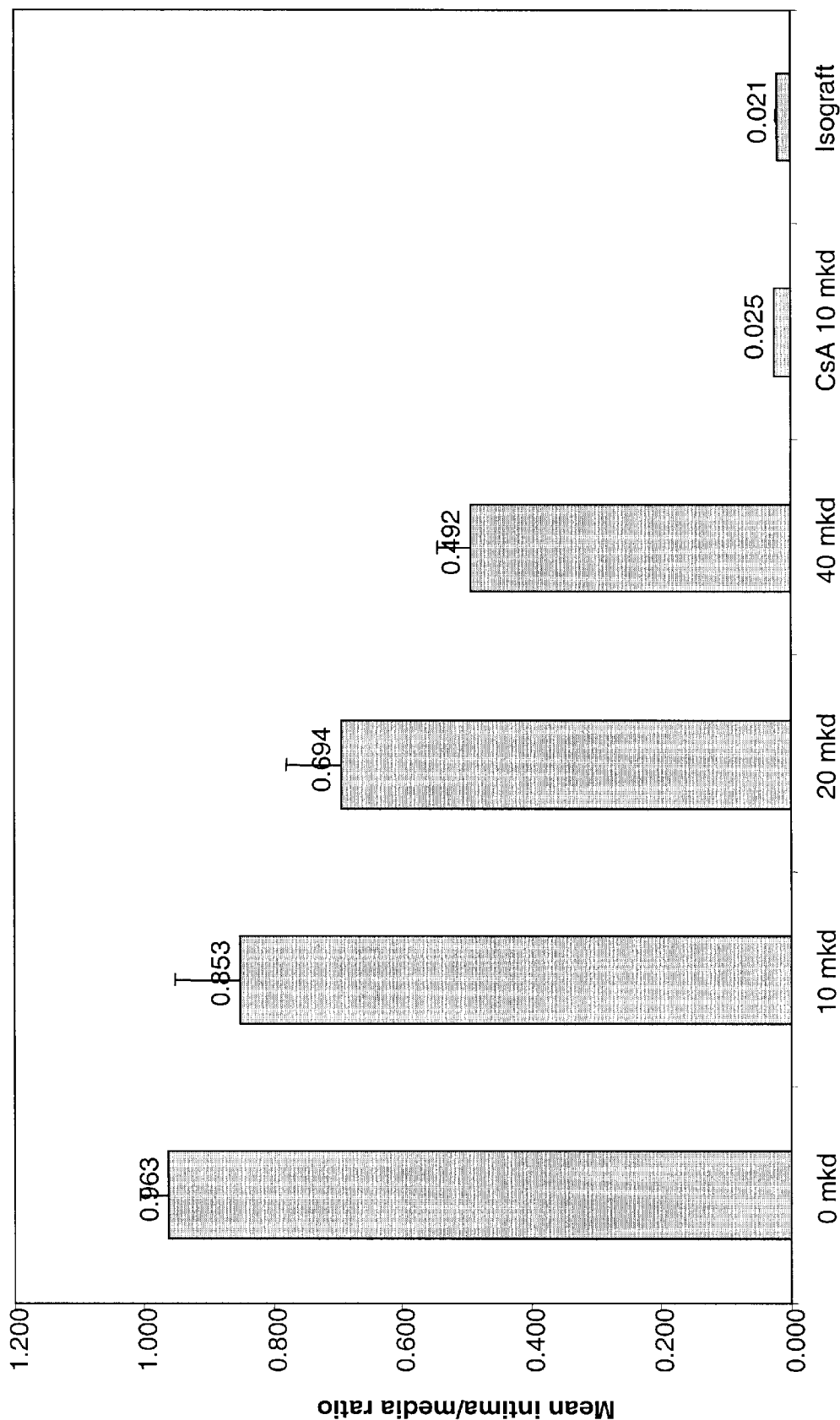

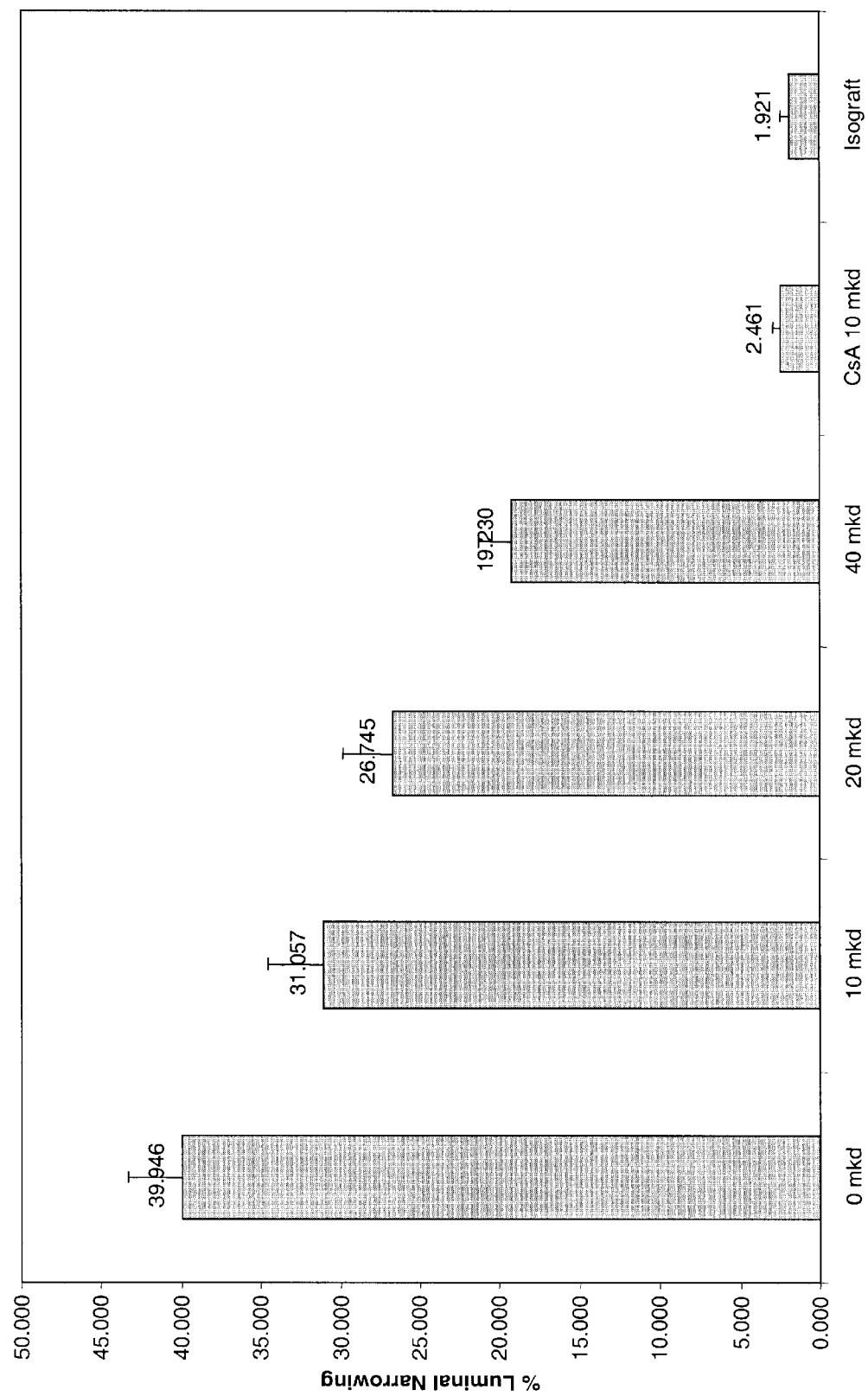

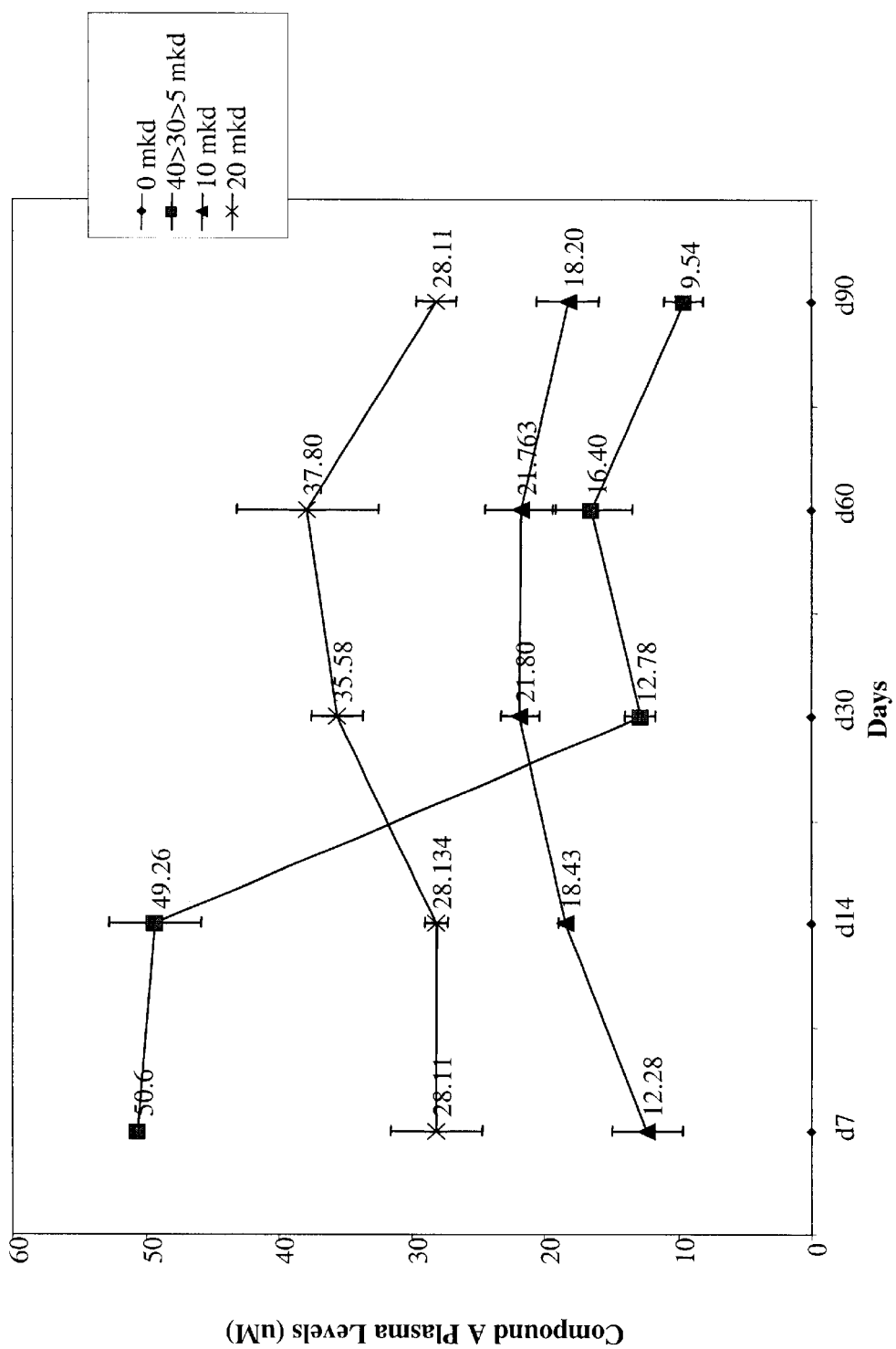

COMPOUNDS AND METHODS FOR TREATING TRANSPLANT REJECTION

This application claims priority to U.S. patent application Ser. No. 09/370,046, filed Aug. 6, 1999 now U.S. Pat. No. 6,548,699, which is a continuation of U.S. patent application Ser. No. 09/079,213 filed May 14, 1998, now U.S. Pat. No. 6,147,250, which claims priority to U.S. patent application Ser. No. 60/047,020 filed May 14, 1997. This application also claims priority, as a continuation-in-part, to U.S. patent application Ser. No. 09/815,262, filed Mar. 21, 2001, and to U.S. patent application Ser. No. 60/191,046, filed Mar. 21, 2000.

BACKGROUND OF THE INVENTION

1. Field of the Invention

The current invention provides compounds, compositions and methods to modulate organ and tissue transplant rejection and prolong the survival of transplanted organs and tissues.

2. Background Art

Organ and tissue transplantation has become a standard surgical procedure. In 1990, 15,000 organ transplantations were performed, and by 1999, this number was up to 21,000. The success of surgical transplantation of organs and tissue is largely dependent on the ability of the clinician to modulate the immune response of the transplant recipient. Specifically the immunological response directed against the transplanted foreign tissue must be controlled if the tissue is to survive and function. Currently, skin, kidney, liver, pancreas, lung and heart are the major organs or tissues with which allogeneic transplantations are performed. It has long been known that the normally functioning immune system of the transplant recipient recognizes the transplanted organ as "non-self" tissue and thereafter mounts an immune response to the presence of the transplanted organ. Left unchecked, the immune response will generate a plurality of cells and proteins that will ultimately result in the loss of biological functioning or the death of the transplanted organ.

This tissue/organ rejection can be categorized into three types: hyperacute, acute and chronic. Hyperacute rejection is essentially caused by circulating antibodies in the blood that are directed against the tissue of the transplanted organ (transplant). Hyperacute rejection can occur in a very short time—often in minutes—and leads to necrosis of the transplant. Acute graft rejection reaction is also immunologically mediated and somewhat delayed compared to hyperacute rejection. The chronic form of graft rejection that can occur years after the transplant is the result of a disease state commonly referred to as Graft Arterial Disease (GAD). GAD is largely a vascular disease characterized by neointimal proliferation of smooth muscle cells and mononuclear infiltrates in large and small vessels. This neointimal growth can lead to vessel fibrosis and occlusion, lessening blood flow to the graft tissue and resulting in organ failure. Current immunosuppressant therapies do not adequately prevent chronic rejection. Most of the gains in survival in the last decade are due to improvements in immunosuppressive drugs that prevent acute rejection. However, chronic rejection losses remain the same and drugs that can prevent it are a critical unmet medical need.

It is additionally known that the transplant-host relationship is not restricted to rejection by the host organism alone; in certain cases an immune reaction originating from the transplant and directed against the host tissue (Graft versus Host Disease (GVHD)) can occur (EP-A-217,206). A differentiation is therefore made between a rejection between transplant and host and between host and transplant.

Tissue and organ transplant recipients are customarily treated with one or more cytotoxic agents in an effort to suppress the transplant recipient's immune response against the transplanted organ or tissue. Current immunosuppressant drugs include: cyclosporin, tacrolimus (FK506), sirolimus (rapamycin), methotrexate, mycophenolic acid (mycophenolate mofetil), everolimus, azathiprine, steroids and NOX-100. All of these drugs have side effects (detailed below) that complicate their long-term use. For example, cyclosporin (cyclosporin A), a cyclic polypeptide consisting of 11 amino acid residues and produced by the fungus species Tolypocladium inflatum Gams, is currently the drug of choice for administration to the recipients of allogeneic kidney, liver, pancreas and heart (i.e., wherein donor and recipient are of the same species of mammals) transplants. However, administration of cyclosporin is not without drawbacks as the drug can cause kidney and liver toxicity as well as hypertension. Moreover, use of cyclosporin can lead to malignancies (such as lymphoma) as well as opportunistic infection due to the "global" nature of the immunosuppression it induces in patients receiving long term treatment with the drug, i.e., the hosts normal protective immune response to pathogenic microorganisms is downregulated thereby increasing the risk of infections caused by these agents.

FK506 (tacrolimus) has also been employed as an immunosuppressive agent as a stand-alone treatment or in combination. Although its immunosuppressive activity is 10–100 times greater than cyclosporin, it still has toxicity issues. Known side effects include kidney damage, seizures, tremors, high blood pressure, diabetes, high blood potassium, headache, insomnia, confusion, seizures, neuropathy, and gout. It has also been associated with miscarriages.

Methotrexate is commonly added to the treatment of the cytotoxic agent. Methotrexate is given in small doses several times after the transplant. Although the combination of cyclosporin and methotrexate has been found to be effective in decreasing the severity of transplant rejection, there are side effects, such as mouth sores and liver damage.

Severe transplant rejection can be treated with steroids. However, the side effects of steroids can be extreme, such as weight gain, fluid retention, elevated blood sugar, mood swings, and/or confused thinking.

Rapamycin, a lipophilic macrolide used as an anti-rejection medication can be taken in conjunction with other anti-rejection medicines (i.e., cyclosporin) to reduce the amount of toxicity of the primary cytotoxic agent, but it too has specific side effects, such as causing high cholesterol, high triglycerides, high blood pressure, rash and acne. Moreover, it has been associated with anemia, joint pain, diarrhea, low potassium and a decrease in blood platelets.

Vitamin D has been employed to decrease bone loss caused by cyclosporin (U.S. Pat. No. 6,071,897) and was shown to decrease the possibility of infection noted by the use of cyclosporin.

Although many approaches have been conceived to treat transplant rejection, there is still room for improvement. (See U.S. Pat. Nos. 6,239,124, 6,071,897, 5,788,968, 5,728,721, 5,308,847, 5,298,523, 5,212,155, 5,100,899 all herein incorporated by reference in their entirety.)

U.S. Pat. No. 5,262,439 to Parthasarathy, which is assigned to AtheroGenics, Inc. discloses analogs of probucol with increased water solubility in which one or both of the hydroxyl groups are replaced with ester groups that increase the water solubility of the compound. In one embodiment, the derivative is selected from the group consisting of a mono- or di-probucol ester of succinic acid, glutaric acid, adipic acid, seberic acid, sebacic acid, azelaic acid, or maleic acid. In another embodiment, the probucol derivative is a mono- or di-ester in which the ester contains an alkyl or alkenyl group that contains a functionality selected from the group consisting of a carboxylic acid group, amine group, salt of an amine group, amide groups, amide groups, and aldehyde groups.

U.S. Pat. No. 6,121,319, which issued on Sep. 19, 2000, and corresponding WO 98/51662 filed by AtheroGenics, Inc. and published on Nov. 18, 1998, describes certain compounds of formula having the structure

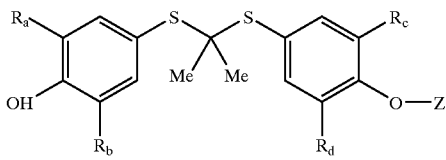

wherein:
$R_a$, $R_b$, $R_c$, and $R_d$ are independently any group that does not otherwise adversely affect the desired properties of the molecule, including hydrogen, straight chained, branched, or cyclic alkyl which may be substituted, aryl, substituted aryl, heteroaryl, substituted heteroaryl, alkaryl, substituted alkaryl, aralkyl or substituted aralkyl; substituents on the $R_a$, $R_b$, $R_c$ and $R_d$ groups are selected from the group consisting of hydrogen, halogen, alkyl, nitro, amino, haloalkyl, alkylamino, dialkylamino, acyl, and acyloxy;

Z is selected from the group consisting of hydrogen, alkyl, substituted alkyl, alkenyl, substituted alkenyl, alkynyl, substituted alkynyl, aryl, aralkyl, alkaryl, heteroaryl, heteroaralkyl, a carbohydrate group, —(CH$_2$)—R$_e$, —C(O)—R$_g$, and —C(O)—(CH$_2$)$_n$—R$_h$, wherein (a) when each of $R_a$, $R_b$, $R_c$, and $R_d$ are t-butyl, Z cannot be hydrogen; and the other variables are as defined in those specifications, for the treatment of disorders mediated by VCAM-1, and inflammatory and cardiovascular disorders.

WO 01/70757 filed by AtheroGenics, Inc. and published on Sep. 27, 2001, describes the use of certain thioethers of the following formula, and pharmaceutically acceptable salts thereof:

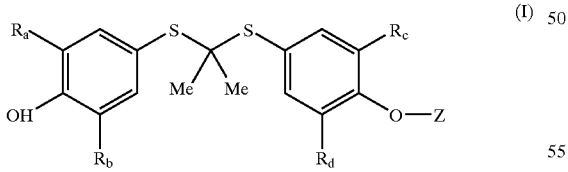

wherein
a) $R_a$, $R_b$, $R_c$, and $R_d$ are independently any group that does not adversely affect the desired properties of the molecule, including hydrogen, alkyl, substituted alkyl, aryl, substituted aryl, heteroaryl, substituted heteroaryl, alkaryl, substituted alkaryl, aralkyl, or substituted aralkyl; and
b) Z is (i) a substituted or unsubstituted carbohydrate, (ii) a substituted or unsubstituted alditol, (iii) C$_{1-10}$alkyl or substituted C$_{1-10}$alkyl, terminated by sulfonic acid, (iv) C$_{1-10}$alkyl or substituted C$_{1-10}$alkyl, terminated by phosphonic acid, (v) substituted or unsubstituted C$_{1-10}$alkyl—O—C(O)—C$_{1-10}$alkyl, (vi) straight chained polyhydroxylated C$_{3-10}$alkyl; (vii)—(CR$_2$)$_{1-6}$—COOH, wherein R is independently hydrogen, halo, amino, or hydroxy, and wherein at least one of the R substituents is not hydrogen; or (viii) —(CR$_2$)$_{1-6}$—X, wherein X is aryl, heteroaryl, or heterocycle, and R is independently hydrogen, halo, amino, or hydroxy.

for use in treating organ transplant rejection.

Given the strong side effects of the current drugs, typically immunosuppressant drugs, that are now commonly used in treating solid organ transplant rejection, there is a strong need to provide new methods in the tissue and transplant field that have low toxicity and are effective in transplant rejection either alone or in combination with known treatment regimens.

BRIEF SUMMARY OF THE INVENTION

The present invention provides a method of inhibiting organ or tissue transplant rejection in a mammal, either alone or in combination with other medications, wherein the method comprises administering a compound of the formula

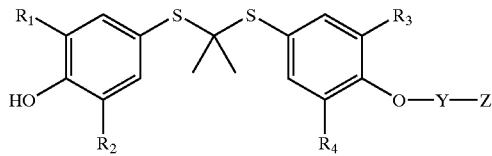

or a pharmaceutically acceptable salt thereof wherein:
Y is a bond or

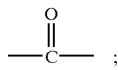

$R_1$, $R_2$, $R_3$, and $R_4$ are independently selected from the group consisting of hydrogen, hydroxy, C$_{1-10}$alkyl, aryl, heteroaryl, C$_{1-10}$alkaryl, and aryl C$_{1-10}$alkyl, wherein all nonhydrogen and hydroxy substituents may optionally be substituted from one or more of the group selected from C$_{1-10}$alkyl, halogen, nitro, amino, haloC$_{1-10}$alkyl, C$_{1-10}$alkylamino, diC$_{1-10}$alkylamino, acyl, and acyloxy;

Z is selected from the group consisting of C$_{1-10}$alkyl, C$_{2-10}$alkenyl, C$_{2-10}$alkynyl, hydroxyC$_{1-10}$alkyl, aryl, heteroaryl, C$_{1-10}$alkaryl, arylC$_{1-10}$alkyl, heteroaryl-C$_{1-10}$alkyl, C$_{1-10}$alkoxyC$_{1-10}$alkyl, C$_{1-10}$alkylamino-C$_{1-10}$alkyl, carboxyC$_{1-10}$alkyl, C$_{1-10}$dialkylamino-C$_{1-10}$alkyl, aminoC$_{1-10}$alkyl, heterocycle, heterocyclC$_{1-10}$alkyl, R$_7$NH, R$_7$R$_7$N, carboxy, carbohydrate group, carbohydrate lactone group, and an alditol group wherein all may optionally be substituted by one or more R$_5$;

R$_5$ is independently selected from the group selected from hydroxy, C$_{1-10}$alkyl, C$_{1-10}$alkoxy, halo, nitro, amino, cyano, C$_{1-10}$alkylamino, diC$_{1-10}$alkylamino, acyl, acyloxy, COOH, COOR$_7$, OC(O)R$_7$, CH(OH)R$_7$, NHR$_7$, NR$_7$R$_7$, C(O)NH$_2$, C(O)NHR$_7$, CONR$_7$R$_7$, NHC(O)O—R$_7$, OSO$_3$H, SO$_3$H, SO$_2$NHR$_7$, SO$_2$NR$_7$R$_7$, P(O)(OH)OR$_7$, PO$_2$H$_2$P(O)(OH)R$_7$, P(O)(OR$_7$)$_2$, P(O)R$_7$(OR$_7$), OPO$_3$H, PO$_3$H$_2$, hydroxymethyl, and cyclic phosphate, wherein when possible, all may be optionally substituted by one or more R$_6$;

$R_6$ is independently selected from the group consisting of hydroxy, $C_{1-10}$alkyl, $C_{1-10}$alkoxy, acyloxy, halo, nitro, amino, cyano, halo$C_{1-10}$alkyl, $C_{1-10}$alkylamino, di$C_{1-10}$alkylamino, acyl, and acyloxy;

$R_7$ is independently selected from the group consisting of $C_{1-10}$alkyl, $C_{2-10}$alkenyl, $C_{2-10}$alkynyl, $C_{1-10}$alkoxy, $C_{1-10}$alkoxycarbonyl$C_{1-10}$alkyl, aryl, carboxy-$C_{1-10}$alkyl, $C_{1-10}$alkylcarboxy$C_{1-10}$alkyl, $C_{1-10}$alkylcarboxy$C_{1-10}$aryl, heterocycle, heterocycl-$C_{1-10}$alkyl, and heteroaryl, wherein all may be optionally substituted by one or more $R_8$; and $R_8$ is independently selected from the group consisting of hydroxy, $C_{1-10}$alkyl, $C_{1-10}$alkoxy, acyloxy, halo, nitro, amino, cyano, and carboxy;

wherein two $R_7$ groups may come together to form a 4 to 7 membered ring.

The present invention also provides a method of moderating transplant rejection and a method to increase transplant survival. Other advantages of the invention will become clearer in light of the detailed description, drawings and claims.

This method can be used to treat tissue/organ rejection categorized as either or a combination of hyperacute, acute and chronic. The invention is particularly useful in treating the chronic form of organ rejection, and in particular Graft Arterial Disease. The method can be used to treat rejection of any organ, and in particular, skin, kidney, liver, pancreas, lung and heart.

The invention also includes pharmaceutical compositions suitable for the treatment of transplant rejection.

BRIEF DESCRIPTION OF THE DRAWINGS

FIG. 1 is a bar chart graph showing the mean intima-to-media ratio measured 90 days post operation versus dosage.

FIG. 2 shows the percent luminal narrowing of the graft section 90 days post operation.

FIG. 3 is a graph of the relative plasma levels of Compound A found in the groups of animals 7, 14, 30, 60, and 90 days after subcutaneous administration in PTC/saline 1:5 vehicle.

DETAILED DESCRIPTION OF THE INVENTION

The present invention addresses the need for an alternate method of treating organ and tissue transplant rejection. The method provides means whereby the rejection of tissue or organs after transplantation can be prevented or controlled, thus prolonging the survival of the tissue or organ. The present invention can be used in hyperacute, acute and chronic rejection of tissue or organs. Combinations of drugs and treatment regimens are also contemplated by the invention.

Many of the compounds used in the invention are described in detail in U.S. Pat. No. 6,147,250, herein incorporated by reference in its entirety.

Suitable compounds of the invention are described by the following formula

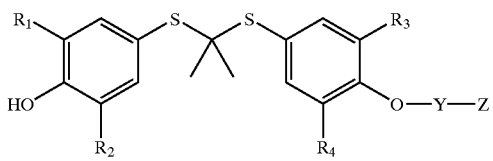

or a pharmaceutically acceptable salt thereof wherein:

Y is a bond or

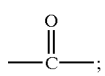

$R_1$, $R_2$, $R_3$, and $R_4$ are independently selected from the group consisting of hydrogen, hydroxy, $C_{1-10}$alkyl, aryl, heteroaryl, $C_{1-10}$alkaryl, and aryl $C_{1-10}$alkyl, wherein all nonhydrogen and hydroxy substituents may optionally be substituted from one or more of the group selected from $C_{1-10}$alkyl, halogen, nitro, amino, halo$C_{1-10}$alkyl, $C_{1-10}$alkylamino, di$C_{1-10}$alkylamino, acyl, and acyloxy;

Z is selected from the group consisting of $C_{1-10}$alkyl, $C_{2-10}$alkenyl, $C_{2-10}$alkynyl, hydroxy$C_{1-10}$alkyl, aryl, heteroaryl, $C_{1-10}$alkaryl, aryl$C_{1-10}$alkyl, heteroaryl$C_{1-10}$alkyl, $C_{1-10}$alkoxy$C_{1-10}$alkyl, $C_{1-10}$alkylamino$C_{1-10}$alkyl, carboxy$C_{1-10}$alkyl, $C_{1-10}$dialkylamino$C_{1-10}$alkyl, amino$C_{1-10}$alkyl, heterocycle, heterocycl$C_{1-10}$alkyl, $R_7$NH, $R_7R_7$N, carboxy, carbohydrate group, carbohydrate lactone group, and an alditol group wherein all may optionally be substituted by one or more $R_5$;

$R_5$ is independently selected from the group selected from hydroxy, $C_{1-10}$alkyl, $C_{1-10}$alkoxy, halo, nitro, amino, cyano, $C_{1-10}$alkylamino, di$C_{1-10}$alkylamino, acyl, acyloxy, COOH, COOR$_7$, OC(O)R$_7$, CH(OH)R$_7$, NHR$_7$, NR$_7$R$_7$, C(O)NH$_2$, C(O)NHR$_7$, CONR$_7$R$_7$, NHC(O)O—R$_7$, OSO$_3$H, SO$_3$H, SO$_2$NHR$_7$, SO$_2$NR$_7$R$_7$, P(O)(OH)OR$_7$, PO$_2$H$_2$P(O)(OH)R$_7$, P(O)(OR$_7$)$_2$, P(O)R$_7$(OR$_7$), OPO$_3$H, PO$_3$H$_2$, hydroxymethyl, and cyclic phosphate, wherein when possible, all may be optionally substituted by one or more $R_6$;

$R_6$ is independently selected from the group consisting of hydroxy, $C_{1-10}$alkyl, $C_{1-10}$alkoxy, acyloxy, halo, nitro, amino, cyano, halo$C_{1-10}$alkyl, $C_{1-10}$alkylamino, di$C_{1-10}$alkylamino, acyl, and acyloxy;

$R_7$ is independently selected from the group consisting of $C_{1-10}$alkyl, $C_{2-10}$alkenyl, $C_{2-10}$alkynyl, $C_{1-10}$alkoxy, $C_{1-10}$alkoxycarbonyl$C_{1-10}$alkyl, aryl, carboxy-$C_{1-10}$alkyl, $C_{1-10}$alkylcarboxy$C_{1-10}$alkyl, $C_{1-10}$alkylcarboxy$C_{1-10}$aryl, heterocycle, heterocycl-$C_{1-10}$alkyl, and heteroaryl, wherein all may be optionally substituted by one or more $R_8$; and $R_8$ is independently selected from the group consisting of hydroxy, $C_{1-10}$alkyl, $C_{1-10}$alkoxy, acyloxy, halo, nitro, amino, cyano, and carboxy;

wherein two $R_7$ groups may come together to form a 4 to 7 membered ring.

In a narrower embodiment, the compound may be chosen from the formula

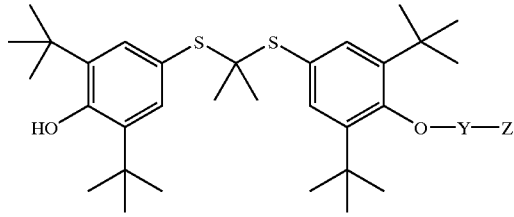

or a pharmaceutically acceptable salt wherein:

Y is a bond;

Z is selected from the group consisting of $C_{1-10}$alkyl, $C_{2-10}$alkenyl, $C_{2-10}$alkynyl, hydroxy$C_{1-10}$alkyl, aryl, heteroaryl, $C_{1-10}$alkaryl, aryl$C_{1-10}$alkyl, heteroaryl-$C_{1-10}$alkyl, $C_{1-10}$alkoxy$C_{1-10}$alkyl, $C_{1-10}$alkylamino-$C_{1-10}$alkyl, carboxy$C_{1-10}$alkyl, $C_{1-10}$dialkylamino-$C_{1-10}$alkyl, amino$C_{1-10}$alkyl, heterocycle, heterocycl$C_{1-10}$alkyl, $R_7$NH, $R_7R_7$N, carbohydrate group, carbohydrate lactone group, and an alditol group wherein all may optionally be substituted by one or more $R_5$;

$R_5$ is independently selected from the group selected from hydroxy, $C_{1-10}$alkyl, $C_{1-10}$alkoxy, halo, nitro, amino, cyano, $C_{1-10}$alkylamino, di$C_{1-10}$alkylamino, acyl, acyloxy, COOH, COOR$_7$, OC(O)R$_7$, CH(OH)R$_7$, NHR$_7$, NR$_7$R$_7$, C(O)NH$_2$, C(O)NHR$_7$, CONR$_7$R$_7$, NHC(O)O—R$_7$, OSO$_3$H, SO$_3$H, SO$_2$NHR$_7$, SO$_2$NR$_7$R$_7$, P(O)(OH)OR$_7$, PO$_2$H$_2$P(O)(OH)R$_7$, P(O)(OR$_7$)$_2$, P(O)R$_7$(OR$_7$), OPO$_3$H, PO$_3$H$_2$, hydroxymethyl, and cyclic phosphate, wherein when possible, all may be optionally substituted by one or more $R_6$;

$R_6$ is independently selected from the group consisting of hydroxy, $C_{1-10}$alkyl, $C_{1-10}$alkoxy, acyloxy, halo, nitro, amino, cyano, halo$C_{1-10}$alkyl, $C_{1-10}$alkylamino, di$C_{1-10}$alkylamino, acyl, and acyloxy;

$R_7$ is independently selected from the group consisting of $C_{1-10}$alkyl, $C_{2-10}$alkenyl, $C_{2-10}$alkynyl, $C_{1-10}$alkoxy, $C_{1-10}$alkoxycarbonyl$C_{1-10}$alkyl, aryl, carboxy-$C_{1-10}$alkyl, $C_{1-10}$alkylcarboxy$C_{1-10}$alkyl, $C_{1-10}$alkylcarboxy$C_{1-10}$aryl, heterocycle, heterocycl-$C_{1-10}$alkyl, and heteroaryl, wherein all may be optionally substituted by one or more $R_8$; and $R_8$ is independently selected from the group consisting of hydroxy, $C_{1-10}$alkyl, $C_{1-10}$alkoxy, acyloxy, halo, nitro, amino, cyano, and carboxy;

wherein two $R_7$ groups may come together to form a 4 to 7 membered ring.

In another embodiment of the above formula, Z is selected from the group consisting of $C_{1-6}$alkyl, hydroxy$C_{1-6}$alkyl, $C_{1-6}$alkoxy$C_{1-6}$alkyl, and carboxy$C_{1-6}$alkyl, wherein all may optionally be substituted by one or more $R_5$;

$R_5$ is independently selected from the group selected from hydroxy, amino, halo, COOH, COOR$_7$, CH(OH)R$_7$, NHR$_7$, NR$_7$R$_7$, C(O)NH$_2$, C(O)NHR$_7$, CONR$_7$R$_7$, OSO$_3$H, SO$_3$H, SO$_2$NHR$_7$, SO$_2$NR$_7$R$_7$, P(O)(OH)OR$_7$, P(O)(OH)R$_7$, P(O)HR$_7$, P(OR$_7$)$_2$, P(O)R$_7$(OR$_7$), OPO$_3$H, PO$_3$H$_2$, and hydroxymethyl, wherein when possible, all may be optionally substituted by one or more $R_6$;

$R_6$ is independently selected from the group consisting of hydroxy, $C_{1-10}$alkyl, $C_{1-10}$alkoxy, acyloxy, halo, nitro, amino, cyano, halo$C_{1-10}$alkyl, $C_{1-10}$alkylamino, di$C_{1-10}$alkylamino, acyl, and acyloxy;

$R_7$ is independently selected from the group consisting of $C_{1-6}$alkyl, $C_{2-10}$alkenyl, $C_{2-6}$alkynyl, $C_{1-6}$alkoxy, $C_{1-6}$alkoxycarbonyl$C_{1-6}$alkyl, carboxy$C_{1-6}$alkyl, and $C_{1-6}$alkylcarboxy$C_{1-6}$alkyl, wherein all may be optionally substituted by one or more $R_8$; and $R_8$ is independently selected from the group consisting of hydroxy, $C_{1-6}$alkyl, $C_{1-6}$alkoxy, acyloxy, halo, amino, cyano, and carboxy.

In another embodiment of the above formula, Z is $C_{1-6}$alkyl, optionally substituted by one or more $R_5$;

$R_5$ is independently selected from the group consisting of halo, COOH, COOR$_7$, CONH$_2$, CONHR$_7$, CONR$_7$R$_7$, and amino;

$R_7$ is independently selected from the group consisting of $C_{1-6}$alkyl, carboxy$C_{1-6}$alkyl, $C_{1-6}$alkoxycarbonyl$C_{1-6}$ alkyl, and $C_{16}$alkylcarboxy$C_{1-6}$alkyl, wherein all may be optionally substituted by one or more $R_8$; and $R_8$ is independently selected from the group consisting of hydroxy, halo, amino, and carboxy.

In another embodiment of the above formula, Z is $C_{1-6}$alkyl, optionally substituted by one or more $R_5$; and $R_5$ is COOH.

Specific compounds of the above formula are

Compound A

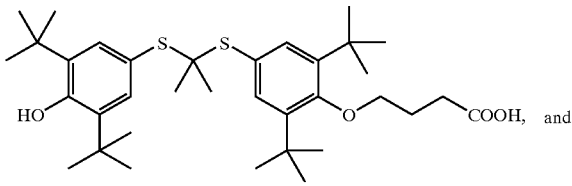

and

Compound B

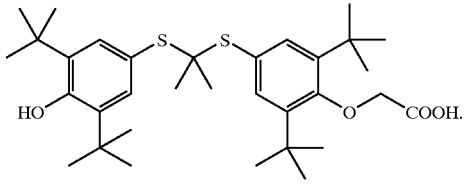

In another embodiment of the above formula, Z is an alditol, optionally substituted with one or more $R_5$; and $R_5$ is independently selected from the group consisting of halo, amino, carboxy, di$C_{1-6}$alkylamino, and $C_{1-6}$alkylamino.

Specific compounds of the above formula are

Compound C

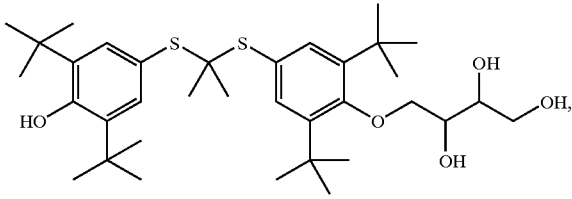

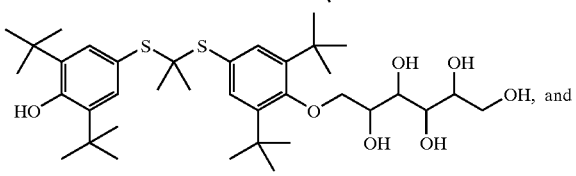

and

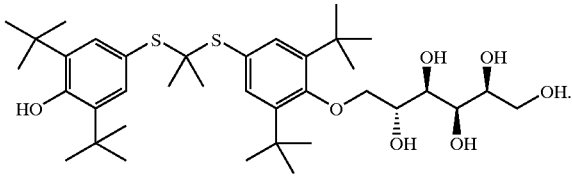

In another embodiment of the above formula, Z is a carbohydrate or a carbohydrate lactone, optionally substituted by one or more $R_5$; and $R_5$ is independently selected from the group consisting of halo, amino, carboxy, di$C_{1-6}$alkylamino, acyloxy, and $C_{1-6}$alkylamino.

Specific compounds of the above formula are

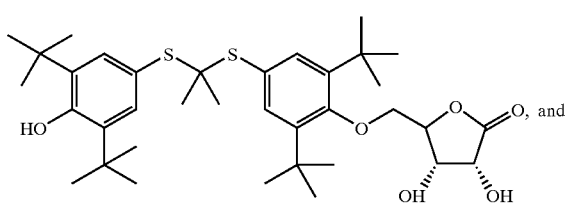

Compound D

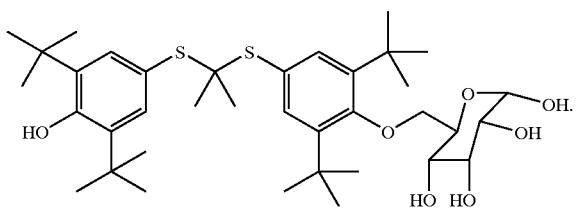

In yet another embodiment of the above formula, Z is selected from the group consisting of $C_{1-6}$alkyl, $C_{1-6}$alkoxy$C_{1-6}$alkyl, $C_{1-6}$alkylamino$C_{1-6}$alkyl, $C_{1-6}$dialkylamino$C_{1-6}$alkyl, and amino$C_{1-6}$alkyl, wherein all may optionally be substituted by one or more $R_5$;

$R_5$ is independently selected from the group selected from hydroxy, $C_{1-6}$alkyl, $C_{1-6}$alkoxy, acyloxy, halo, nitro, amino, cyano, $C_{1-6}$alkylamino, di$C_{1-6}$alkylamino, acyl, acyloxy, COOH, COOR$_7$, OC(O)R$_7$, CH(OH)R$_7$, NHR$_7$, NR$_7$R$_7$, C(O)NH$_2$, C(O)NHR$_7$, CONR$_7$R$_7$, NHC(O)O—R$_7$, OSO$_3$H, SO$_3$H, SO$_2$NHR$_7$, SO$_2$NR$_7$R$_7$, P(O)(OH)OR$_7$, P(O)HR$_7$, P(O)(OH)R$_7$, P(OR$_7$)$_2$, P(O)R$_7$(OR$_7$), OPO$_3$H, PO$_3$H$_2$, hydroxymethyl, and cyclic phosphate, wherein when possible, all may be optionally substituted by one or more $R_6$;

$R_6$ is independently selected from the group consisting of hydroxy, $C_{1-6}$alkyl, $C_{1-6}$alkoxy, acyloxy, halo, amino, cyano, halo$C_{1-6}$alkyl, $C_{1-6}$alkylamino, di$C_{1-6}$alkylamino, acyl, and acyloxy;

$R_7$ is independently selected from the group consisting of $C_{1-6}$alkyl, $C_{2-10}$alkenyl, $C_{2-10}$alkynyl, $C_{1-10}$alkoxy, $C_{1-10}$alkoxycarbonyl$C_{1-10}$alkyl, carboxy$C_{1-6}$alkyl, $C_{1-6}$alkylcarboxy$C_{1-6}$alkyl, and heteroaryl, wherein all may be optionally substituted by one or more $R_8$; and $R_8$ is independently selected from the group consisting of hydroxy, halo, amino, and carboxy Specifically, the compound may be chosen from

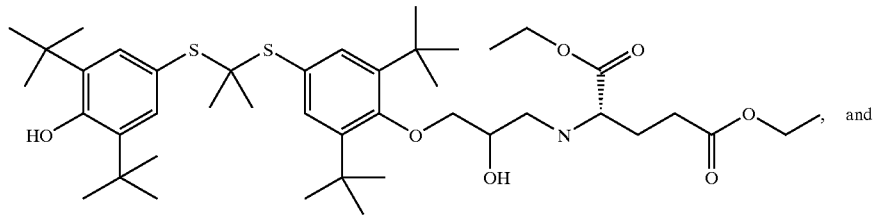

Compound E

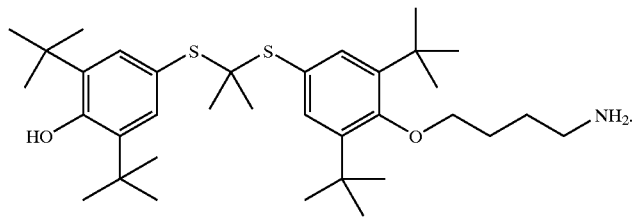

Compound F

In another embodiment of the above formula, Z is selected from the group consisting of $C_{1-6}$alkyl, aryl, heteroaryl, $C_{1-6}$alkaryl, aryl$C_{1-6}$alkyl, heteroaryl$C_{1-6}$alkyl, heterocycle, and heterocycl$C_{1-6}$alkyl, wherein all may optionally be substituted by one or more $R_5$;

$R_5$ is independently selected from the group selected from hydroxy, $C_{1-6}$alkyl, $C_{1-6}$alkoxy, acyloxy, halo, nitro, amino, cyano, $C_{1-6}$alkylamino, di$C_{1-6}$alkylamino, acyl, acyloxy, COOH, COOR$_7$, OC(O)R$_7$, CH(OH)R$_7$, NHR$_7$, NR$_7$R$_7$, C(O)NH$_2$, C(O)NHR$_7$, CONR$_7$R$_7$, NHC(O)O—R$_7$, OSO$_3$H, SO$_3$H, SO$_2$NHR$_7$, SO$_2$NR$_7$R$_7$, P(O)(OH)OR$_7$, P(O)HR$_7$, P(O)(OH)R$_7$)$_2$, P(O)R$_7$(OR$_7$), OPO$_3$H, PO$_3$H$_2$, hydroxymethyl, and cyclic phosphate, wherein when possible, all may be optionally substituted by one or more $R_6$;

$R_6$ is independently selected from the group consisting of hydroxy, $C_{1-6}$alkyl, $C_{1-6}$alkoxy, acyloxy, halo, amino, cyano, halo$C_{1-6}$alkyl, $C_{1-6}$alkylamino, di$C_{1-6}$ alkylamino, acyl, and acyloxy;

$R_7$ is independently selected from the group consisting of $C_{1-6}$alkyl, $C_{2-10}$alkenyl, $C_{2-10}$alkynyl, $C_{1-10}$alkoxy, $C_{1-10}$alkoxycarbonyl$C_{1-10}$alkyl, aryl, carboxy$C_{1-6}$alkyl, $C_{1-6}$alkylcarboxy$C_{1-6}$alkyl, $C_{1-6}$alkylcarboxy-$C_{1-6}$aryl, heterocycle, heterocycl$C_{1-6}$alkyl, and heteroaryl, wherein all may be optionally substituted by one or more $R_8$; and $R_8$ is independently selected from the group consisting of hydroxy, halo, amino, and carboxy;

wherein two $R_7$ groups may come together to form a 4 to 7 membered ring.

In another embodiment of the invention, the compound may be chosen from the following formula

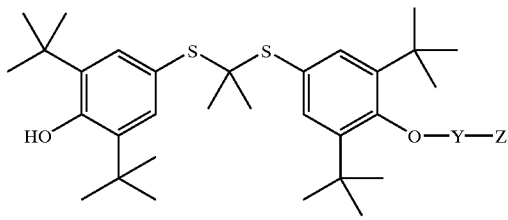

or a pharmaceutically acceptable salt wherein:

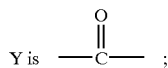

Y is

Z is selected from the group consisting of $C_{1-10}$alkyl, $C_{2-10}$alkenyl, $C_{2-10}$alkynyl, hydroxy$C_{1-10}$alkyl, aryl, heteroaryl, $C_{1-10}$alkaryl, aryl$C_{1-10}$alkyl, heteroaryl-$C_{1-10}$alkyl, $C_{1-10}$alkoxy$C_{1-10}$alkyl, $C_{1-10}$alkylamino-$C_{1-10}$alkyl, carboxy$C_{1-10}$alkyl, $C_{1-10}$dialkylamino-$C_{1-10}$alkyl, amino$C_{1-10}$alkyl, heterocycle, heterocycl$C_{1-10}$alkyl, $R_7$NH, $R_7R_7$N, carboxy, carbohydrate group, carbohydrate lactone group, and an alditol group wherein all may optionally be substituted by one or more $R_5$;

$R_5$ is independently selected from the group selected from hydroxy, $C_{1-10}$alkyl, $C_{1-10}$alkoxy, halo, nitro, amino, cyano, $C_{1-10}$alkylamino, di$C_{1-10}$alkylamino, acyl, acyloxy, COOH, COOR$_7$, OC(O)R$_7$, CH(OH)R$_7$, NHR$_7$, NR$_7$R$_7$, C(O)NH$_2$, C(O)NHR$_7$, CONR$_7$R$_7$, NHC(O)O—R$_7$, OSO$_3$H, SO$_3$H, SO$_2$NHR$_7$, SO$_2$NR$_7$R$_7$, P(O)(OH)OR$_7$, PO$_2$H$_2$P(O)(OH)R$_7$, P(O)(OR$_7$)$_2$, P(O)R$_7$(OR$_7$), OPO$_3$H, PO$_3$H$_2$, hydroxymethyl, and cyclic phosphate, wherein when possible, all may be optionally substituted by one or more $R_6$;

$R_6$ is independently selected from the group consisting of hydroxy, $C_{1-10}$alkyl, $C_{1-10}$alkoxy, acyloxy, halo, nitro, amino, cyano, halo$C_{1-10}$alkyl, $C_{1-10}$alkylamino, di$C_{1-10}$alkylamino, acyl, and acyloxy;

$R_7$ is independently selected from the group consisting of $C_{1-10}$alkyl, $C_{2-10}$alkenyl, $C_{2-10}$alkynyl, $C_{1-10}$alkoxy, $C_{1-10}$alkoxycarbonyl$C_{1-10}$alkyl, aryl, carboxy-$C_{1-10}$alkyl, $C_{1-10}$alkylcarboxy$C_{1-10}$alkyl, $C_{1-10}$alkylcarboxy$C_{1-10}$aryl, heterocycle, heterocycl-$C_{1-10}$alkyl, and heteroaryl, wherein all may be optionally substituted by one or more $R_8$; and $R_8$ is independently selected from the group consisting of hydroxy, $C_{1-10}$alkyl, $C_{1-10}$alkoxy, acyloxy, halo, nitro, amino, cyano, and carboxy;

wherein two $R_7$ groups may come together to form a 4 to 7 membered ring.

In another embodiment of the above formula, Z is selected from the group consisting of $C_{1-6}$alkyl, hydroxy$C_{1-6}$alkyl, $C_{1-6}$alkoxy$C_{1-6}$alkyl, and carboxy$C_{1-6}$alkyl, wherein all may optionally be substituted by one or more $R_5$;

$R_5$ is independently selected from the group selected from hydroxy, amino, halo, COOH, COOR$_7$, CH(OH)R$_7$, NHR$_7$, NR$_7$R$_7$, C(O)NH$_2$, C(O)NHR$_7$, CONR$_7$R$_7$, OS$_3$H, SO$_3$H, SO$_2$NHR$_7$, SO$_2$NR$_7$R$_7$, P(O)(OH)OR$_7$, P(O)(OH)R$_7$, P(O)HR$_7$, P(OR$_7$)$_2$, P(O)R$_7$(OR$_7$), OPO$_3$H, PO$_3$H$_2$, and hydroxymethyl, wherein when possible, all may be optionally substituted by one or more $R_6$;

$R_7$ is independently selected from the group consisting of $C_{1-6}$alkyl, $C_{2-10}$alkenyl, $C_{2-6}$alkynyl, $C_{1-6}$alkoxy, $C_{1-6}$alkoxycarbonyl$C_{1-6}$alkyl, carboxy$C_{1-6}$alkyl, and $C_{1-6}$alkylcarboxy$C_{1-6}$alkyl, wherein all may be optionally substituted by one or more $R_8$; and $R_8$ is independently selected from the group consisting of hydroxy, $C_{1-6}$alkyl, $C_{1-6}$alkoxy, acyloxy, halo, amino, cyano, and carboxy.

In another embodiment of the above formula c, Z is $C_{1-6}$alkyl, optionally substituted by one or more $R_5$;

$R_5$ is independently selected from the group consisting of halo, COOH, COOR$_7$, CONH$_2$, CONHR$_7$, CONR$_7$R$_7$, and amino;

$R_7$ is independently selected from the group consisting of $C_{1-6}$alkyl, carboxy$C_{1-6}$alkyl, and $C_{1-6}$alkylcarboxy$C_{1-6}$alkyl, wherein all may be optionally substituted by one or more $R_8$; and $R_8$ is independently selected from the group consisting of hydroxy, halo, amino, and carboxy.

In another embodiment of the above formula, Z is $C_{1-6}$alkyl, optionally substituted by one or more $R_5$; and $R_5$ is COOH.

Specifically, the compound may be chosen from

Compound G

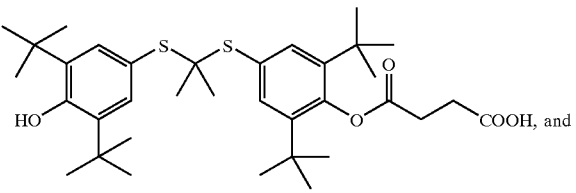

COOH, and

Compound H

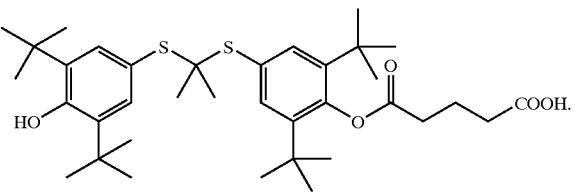

COOH.

In another embodiment of the above formula, Z is selected from the group consisting of $C_{1-6}$alkyl, $C_{1-6}$alkoxy$C_{1-6}$alkyl, $C_{1-6}$alkylamino$C_{1-6}$alkyl, and amino$C_{1-6}$alkyl, wherein all may optionally be substituted by one or more $R_5$;

$R_5$ is independently selected from the group selected from hydroxy, $C_{1-6}$alkyl, $C_{1-6}$alkoxy, acyloxy, halo, nitro, amino, cyano, $C_{1-6}$alkylamino, di$C_{1-6}$alkylamino, acyl, acyloxy, COOH, COOR$_7$, OC(O)R$_7$, CH(OH)R$_7$, NHR$_7$, NR$_7$R$_7$, C(O)NH$_2$, C(O)NHR$_7$, CONR$_7$R$_7$, NHC(O)O—R$_7$, OSO$_3$H, SO$_3$H, SO$_2$NHR$_7$, SO$_2$NR$_7$R$_7$, P(O)(OH)OR$_7$, P(O)HR$_7$, P(O)(OH)R$_7$, P(OR$_7$)$_2$, P(O)R$_7$(OR$_7$), OPO$_3$H, PO$_3$H$_2$, hydroxymethyl, and cyclic phosphate, wherein when possible, all may be optionally substituted by one or more R$_6$;

R$_6$ is independently selected from the group consisting of hydroxy, C$_{1-6}$alkyl, C$_{1-6}$alkoxy, acyloxy, halo, amino, cyano, haloC$_{1-6}$alkyl, C$_{1-6}$alkylamino, diC$_{1-6}$alkylamino, acyl, and acyloxy;

R$_7$ is independently selected from the group consisting of C$_{1-6}$alkyl, C$_{2-10}$alkenyl, C$_{2-10}$alkynyl, C$_{1-10}$alkoxy, C$_{1-10}$alkoxycarbonylC$_{1-10}$alkyl, carboxyC$_{1-6}$alkyl, C$_{1-6}$alkylcarboxyC$_{1-6}$alkyl, and heteroaryl, wherein all may be optionally substituted by one or more R$_8$; and R$_8$ is independently selected from the group consisting of hydroxy, halo, amino, and carboxy In another embodiment of the above formula, the compound may be

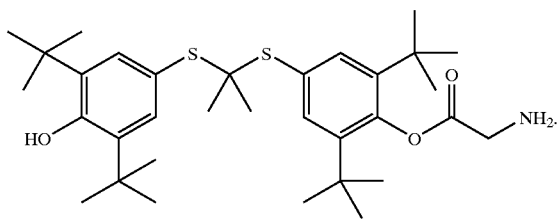

Compound I

In another embodiment of the above formula, Z is selected from the group consisting of C$_{1-6}$alkyl, aryl, heteroaryl, C$_{1-6}$alkaryl, arylC$_{1-6}$alkyl, heteroarylC$_{1-6}$alkyl, heterocycle, and heterocyclC$_{1-6}$alkyl, wherein all may optionally be substituted by one or more R$_5$;

R$_5$ is independently selected from the group selected from hydroxy, C$_{1-6}$alkyl, C$_{1-6}$alkoxy, acyloxy, halo, nitro, amino, cyano, C$_{1-6}$alkylamino, diC$_{1-6}$alkylamino, acyl, acyloxy, COOH, COOR$_7$, OC(O)R$_7$, CH(OH)R$_7$, NHR$_7$, NR$_7$R$_7$, C(O)NH$_2$, C(O)NHR$_7$, CONR$_7$R$_7$, NHC(O)O—R$_7$, OSO$_3$H, SO$_3$H, SO$_2$NHR$_7$, SO$_2$NR$_7$R$_7$, P(O)(OH)OR$_7$, P(O)HR$_7$, P(O)(OH)R$_7$)$_2$, P(O)R$_7$(OR$_7$), OPO$_3$H, PO$_3$H$_2$, hydroxymethyl, and cyclic phosphate, wherein when possible, all may be optionally substituted by one or more R$_6$;

R$_6$ is independently selected from the group consisting of hydroxy, C$_{1-6}$alkyl, C$_{1-6}$alkoxy, acyloxy, halo, amino, cyano, haloC$_{1-6}$alkyl, C$_{1-6}$alkylamino, diC$_{1-6}$alkylamino, acyl, and acyloxy;

R$_7$ is independently selected from the group consisting of C$_{1-6}$alkyl, C$_{2-10}$alkenyl, C$_{2-10}$alkynyl, C$_{1-10}$alkoxy, C$_{1-10}$alkoxycarbonylC$_{1-10}$alkyl, aryl, carboxyC$_{1-6}$alkyl, C$_{1-6}$alkylcarboxyC$_{1-6}$alkyl, C$_{1-6}$alkylcarboxy-C$_{1-6}$aryl, heterocycle, heterocyclC$_{1-6}$alkyl, and heteroaryl, wherein all may be optionally substituted by one or more R$_8$; and R$_8$ is independently selected from the group consisting of hydroxy, halo, amino, and carboxy;

wherein two R$_7$ groups may come together to form a 4 to 7 membered ring.

The term "alkyl", alone or in combination, means an acyclic, saturated straight, branched, or cyclic, primary, secondary, or tertiary hydrocarbon, including those containing from 1 to 10 carbon atoms or from 1 to 6 carbon atoms. Said alkyl radicals may be optionally substituted with groups as defined below. Examples of such radicals include methyl, ethyl, chloroethyl, hydroxyethyl, n-propyl, oxopropyl, isopropyl, n-butyl, cyanobutyl, isobutyl, sec-butyl, tert-butyl, pentyl, aminopentyl, iso-amyl, hexyl, octyl and the like.

The term "alkylene" radical denotes linear or branched radicals including having from 2 to 10 carbon atoms or 2 to 6 carbon atoms and having attachment points for two or more covalent bonds. Examples of such radicals are methylene, ethylene, methylethylene, and isopropylidene.

The term "alkynyl" refers to an unsaturated, acyclic hydrocarbon radical, linear or branched, in so much as it contains one or more triple bonds, including such radicals containing about 2 to 10 carbon atoms or having from 2 to 6 carbon atoms. Said alkynyl radicals may be optionally substituted with groups as defined below. Examples of suitable alkynyl radicals include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, hexyn-3-yl, 3,3-dimethylbutyn-1-yl radicals and the like.

The term "acyl", alone or in combination, means a carbonyl or thionocarbonyl group bonded to a radical selected from, for example, hydrido, alkyl, alkenyl, alkynyl, haloalkyl, alkoxy, alkoxyalkyl, haloalkoxy, aryl, heterocyclyl, heteroaryl, alkylsulfinylalkyl, alkylsulfonylalkyl, aralkyl, cycloalkyl, cycloalkylalkyl, cycloalkenyl, alkylthio, arylthio, amino, alkylamino, dialkylamino, aralkoxy, arylthio, and alkylthioalkyl. Examples of "acyl" are formyl, acetyl, benzoyl, trifluoroacetyl, phthaloyl, malonyl, nicotinyl, and the like.

The terms "alkoxy" and "alkoxyalkyl" embrace linear or branched oxy-containing radicals each having alkyl portions of one to about ten carbon atoms, such as methoxy radical. The term "alkoxyalkyl" also embraces alkyl radicals having one or more alkoxy radicals attached to the alkyl radical, that is, to form monoalkoxyalkyl and dialkoxyalkyl radicals. Other alkoxy radicals are "lower alkoxy" radicals having one to six carbon atoms. Examples of such radicals include methoxy, ethoxy, propoxy, butoxy and tert-butoxy alkyls. The "alkoxy" radicals may be further substituted with one or more halo atoms, such as fluoro, chloro or bromo, to provide "haloalkoxy" radicals. Examples of such radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy.

The term "alkylamino" denotes "monoalkylamino" and "dialkylamino" containing one or two alkyl radicals, respectively, attached to an amino radical. The terms arylamino denotes "monoarylamino" and "diarylamino" containing one or two aryl radicals, respectively, attached to an amino radical. The term "Aralkylamino", embraces aralkyl radicals attached to an amino radical. The term aralkylamino denotes "monoaralkylamino" and "diaralkylamino" containing one or two aralkyl radicals, respectively, attached to an amino radical. The term aralkylamino further denotes "monoaralkyl monoalkylamino" containing one aralkyl radical and one alkyl radical attached to an amino radical.

The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. Said "aryl" group may have 1 to 3 substituents termed "heteroaryl" such as heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboalkoxy, carboaralkoxy, cyano, and carbohaloalkoxy.

The term "heterocyclic" alone or in combination refers to a nonaromatic cyclic group that can include alkyl moieties which may be substituted, and wherein there is at least one heteroatom, such as oxygen, sulfur, nitrogen, or phosphorus in the ring. Nonlimiting examples are morpholine, piperidine, piperazine, pyrrolidine, azetidine, and tetrahydrofuran. The heterocyclic group can be optionally substituted with one or more moieties selected from the group consisting of hydroxyl, acyl, amino, alkylamino, arylamino, alkoxy, aryloxy, nitro, cyano, sulfonic acid, sulfate, phophonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991, hereby incorporated by reference.

The term "alditol" as referred to herein, and unless otherwise specified, refers to a carbohydrate in which the aldehyde or ketone group has been reduced to an alcohol moiety. The alditols of the present invention can also be optionally substituted or deoxygenated at one or more positions. Exemplary substituents include hydrogen, halo, haloalkyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, thioester, thioether, oxime, hydrazine, carbamate, phosphonic acid, phosphonate, or any other viable functional group that does not inhibit the pharmacological activity of this compound. Particular exemplary substituents include amine and halo, particularly fluorine. The substituent or alditol can be either unprotected, or protected as necessary, as known to those skilled in the art, for example, as taught in Greene, et al., Protective Groups in Organic Synthesis, John Wiley and Sons, Second Edition, 1991, hereby incorporated by reference. The alditol may comprise 3, 4, 5, 6, or 7 carbons. Examples of useful alditols are those derived from reduction of monosaccharides, including specifically those derived from the reduction of pyranose and furanose sugars.

The term "carbohydrate" as referred to herein, and unless otherwise specified, refers to a compound of carbon, hydrogen, and oxygen that contains an aldehyde or ketone group in combination with at least two hydroxyl groups. The term "carbohydrate lactone" represents a carbohydrate, wherein the anomeric hydroxy group has been formally oxidized to a carbonyl group thus forming a substituted or unsubstituted cyclic ester or lactone. The carbohydrates and carbohydrate lactones of the present invention can also be optionally substituted or deoxygenated at one or more positions. Carbohydrates and carbohydrate lactones thus include substituted and unsubstituted monosaccharides, disaccharides, oligosaccharides, and polysaccharides. The saccharide can be an aldose or ketose, and may comprise 3, 4, 5, 6, or 7 carbons. In one embodiment they are monosaccharides. In another embodiment they can be pyranose and furanose sugars. They can be optionally deoxygenated at any corresponding C-position, and/or substituted with one or more moieties such as hydrogen, halo, haloalkyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, thioester, thioether, oxime, hydrazine, carbamate, The term "carbonyl" or

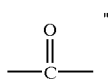

denotes a carbon radical having two of the four covalent bonds shared with an oxygen atom. The term "carboxy" embraces a hydroxyl radical, attached to one of two unshared bonds in a carbonyl group. The term "aldoxy carbonyl" denotes a carbon radical having two of the four covalent bonds shared with an oxygen atom, and a third covalent bond shared with another oxygen, also denoted by

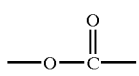

phosphonic acid, phosphonate, or any other viable functional group that does not inhibit the pharmacological activity of this compound. Particular exemplary substituents include amine and halo, particularly fluorine. The substituent, carbohydrate, or carbohydrate lactone can be either unprotected, or protected as necessary, as known to those skilled in the art, for example, as taught in Greene, et al., Protective Groups in Organic Synthesis, John Wiley and Sons, Second Edition, 1991, hereby incorporated by reference.

The term "carboxyalkyl" denotes a carboxy group attached to an alkyl group.

The term "alkoxycarbonyl" denotes a radical having the formula alkyl—O—C(O)—, wherein alkyl is defined herein.

The term "cyano" radical denotes a carbon radical having three of four covalent bonds shared by a nitrogen atom.

The term "halo" and "halogen" means halogens such as fluorine, chlorine, bromine or iodine atoms.

The term "hydroxyalkyl" embraces radicals wherein any one or more of the alkyl carbon atoms is substituted with a hydroxyl. Specifically embraced are monohydroxyalkyl, dihydroxyalkyl and polyhydroxyalkyl radicals.

The term "aralkyl" as used herein, and unless otherwise specified, refers to an aryl group as defined above linked to the molecule through an alkyl group as defined above.

The term "alkoxy" as used herein, and unless otherwise specified, refers to a moiety of the structure—O—alkyl, wherein alkyl is as defined above.

The term "amino" includes primary, secondary, and tertiary amines. An amino moiety can be represented generally by the formula—$NR^1R^2$, wherein $R^1$ and $R^2$ are independently hydrogen or substituted or unsubstituted alkyl.

The term "aminoalkyl" denotes an amino group attached to an alkyl group, for example—alkyl-$NH_2$.

The term "therapeutically effective amount" shall mean that amount of drug or pharmaceutical agent that will elicit the biological or medical response of a tissue, system, animal or human that is being sought.

The term "pharmaceutically acceptable salts" refer to salts or complexes that retain the desired biological activity of the compounds of the present invention and exhibit minimal undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalcturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like. Also included in this definition are pharmaceutically acceptable quaternary salts known by those skilled in the art, which specifically include the quaternary ammonium salt of the formula —NR$^+$A$^-$, wherein R is as defined above and A is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

It is appreciated that compounds of the present invention having a chiral center may exist in and be isolated in optically active and racemic forms. Some compounds may exhibit polymorphism. It is to be understood that the present invention encompasses any racemic, optically-active, diastereomeric, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Examples of methods to obtain optically active materials are known in the art, and include at least the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

Some of the compounds of the present invention can exist in tautomeric, geometric or stereoisomeric forms. The present invention contemplates all such compounds, including cis- and trans-geometric isomers, E- and Z-geometric isomers, R- and S-enantiomers, diastereomers, d-isomers, l-isomers, the racemic mixtures thereof and other mixtures thereof, as falling within the scope of the invention. Pharmaceutically acceptable sales of such tautomeric, geometric or stereoisomeric are also included within the invention. The terms "cis" and "trans" denote a form of geometric isomerism in which two carbon atoms connected by a double bond will each have two high ranking groups on the same side of the double bond ("cis") or on opposite sides of the double bond ("trans"). Some of the compounds described contain alkenyl groups, and are meant to include both cis and trans or "E" and "Z" geometric forms. Some of the compounds described contain one or more stereocenters and are meant to include R, S, and mixtures of R and S forms for each stereocenter present.

Some of the compounds described herein may contain one or more ketonic or aldehydic carbonyl groups or combinations thereof alone or as part of a heterocyclic ring system. Such carbonyl groups may exist in part or principally in the "keto" form and in part or principally as one or more "enol" forms of each aldehyde and ketone group present. Compounds of the present invention having aldehydic or ketonic carbonyl groups are meant to include both "keto" and "enol" tautomeric forms.

Some of the compounds described herein may contain one or more imine or enamine groups or combinations thereof. Such groups may exist in part or principally in the "imine" form and in part or principally as one or more "enamine" forms of each group present. Compounds of the present invention having said imine or enamine groups are meant to include both "imine" and "enamine" tautomeric forms.

While it may be possible for the compounds of the invention to be administered as the raw chemical, it is preferable to present them as a pharmaceutical composition. According to a further aspect, the present invention provides a pharmaceutical composition comprising a compound of the invention or a pharmaceutically acceptable salt or solvate thereof, together with one or more pharmaceutically acceptable carriers thereof and optionally one or more other therapeutic ingredient. The carrier(s) must be acceptable in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of the invention or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampuls and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds of the invention may be administered orally or via injection at a dose of from 0.001 to 2500 mg/kg per day. The dose range for humans is generally from 0.005 mg to 10 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

The compounds of the invention are preferably administered orally or by injection (intravenous or subcutaneous).

The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

The above compounds may be administered alone or in combination with other therapeutic drugs, including those used in connection with organ rejection therapy and particularly including an immunosupressant or other drug mentioned in the Background of the Invention. Specifically, the above compounds may be administered with one or more drug selected from cyclosporin, tacrolimus (FK506), sirolimus (rapamycin), methotrexate, mycophenolic acid (mycophenolate mofetil), everolimus, azathiprine, steroids and NOX-100.

In addition, the above compounds are useful in the treatment of congestive heart failure, multiple sclerosis, systemic lupus, erythematosis, inflammatory bowel disease (IBD), autoimmune diabetes, diabetic vasculopathies (including diabetic retinopathy and diabetic nephropathy), rhinitis, ischemia-reperfusion injury, cystic fibrosis, chronic obstructive pulmonary disease, glomerulonephritis, bronchial asthma, rheumatoid arthritis, Graves disease, gastrointestinal allergies, and conjunctivitis.

The compounds of the present invention may also be administered by use of an intraluminal stent. Although stents are commonly used as part of an angioplasty procedure, intraluminal stents can be used to maintain or control any bodily luminal opening. The compound of the present invention could be used alone or as part of a composition allowing for a controlled release of the therapeutically active compound. The compounds could be coated on the stent or made a part of the stent. They may be layered so as to provide limited release of the active compound, or used in any manner known in the art. See U.S. patent application Nos. 20010029660 and 20010032014, herein incorporated by reference in their entirety.

EXAMPLE 1

Methods for the preparation of the compounds of the invention are disclosed in U.S. Pat. No. 6,147,250. The following is a method of producing Compound A.

Probucol (5, 9.69 mmol) and methyl 4-chlorobutyrate (3.1 g. 1.4 eq) were stirred in DMF (15 mL) and potassium fluoride on alumina (7 g, 5 eq) was added. The mixture was stirred at room temperature under nitrogen for 20.5 hours. It was filtered, diluted with ethyl acetate (100 mL), washed with water and brine, dried over sodium sulfate, and evaporated. Chromatography (MPLC, 10% to 80% of dichloromethane in hexanes) gave 0.98 g of methyl 4-[4-[[1-[[3,5-bis(1,1-dimethylethyl)-4-hydroxyphenyl]thio]-1-methylethyl]thio]-2,6-bis(1,1-dimethylethyl)phenoxy]butyrate.

Methyl 4-[4-[[1-[[3,5-bis(1,1-dimethylethyl)-4-hydroxyphenyl]thio]-1-methylethyl]thio]-2,6-bis(1,1-dimethylethyl)phenoxy]butyrate (0.95 g, obtained above) was dissolved in THI/MeOH/H2O (4:1;1, 15.4 mL) and lithium hydroxide hydrate (0.19 g) was added. The mixture was stirred at room temperature for four hours and then acidified with 0.3 N HCl. The mixture was poured into brine and extracted with ethyl acetate. The organic phase was dried over sodium sulfate and evaporated to give 0.60 g of 4-[4-[[1-[[3,5-bis(1,1-dimethylethyl)-4-hydroxyphenyl]thio]-1-methylethyl]thio]-2,6-bis(1,1-dimethylethyl)phenoxy]butyric acid (Compound A) as a solid.

EXAMPLE 2

Smooth Muscle Cell Inhibition

Cultured human aortic smooth muscle cells (AoSMC) were obtained from Clonetics, Inc. and were used below passage 10. Cells were seeded in 24-well plates. When cells were 80% confluent, they were made quiescent by adding media containing 0.2% serum (as compared to 5% serum in normal culture media) for 48 hours. The cells were then stimulated by 5% serum in the presence or absence of compounds dissolved in DMSO. To establish a dose curve and $IC_{50}$ for each compound, multiple concentrations (20, 15, 10, 5 $\mu$M) were used. Rapamycin (at 1 and 0.1 $\mu$M) was used as a positive control for the assay. After a 20 hr incubation with or without test compounds, $^3$H-thymidine (0.5 $\mu$Ci/per well) was added to the cells for 4 hours of labeling. Washed cells were then lysed in NaOH and the amount of $^3$H-thymidine incorporation was determined by a scintillation counter. Table 1 contains the $IC_{50}$s for compounds A–I.

TABLE 1

| Compound | SMC Proliferation Inhibition ($IC_{50}$) |
|---|---|
| A | 5.5 |
| B | 7 |
| C | 7.2 |
| D | 6 |
| E | 3.7 |
| I | 8 |

EXAMPLE 3

Rat Aortic Allograft Model

Compound A was evaluated for graft arteriosclerosis resulting from aortic heterotropic transplantation. This is a model of graft arteriopathy which is the major obstacle to long term success of solid organ transplantation.

Donor descending aortas from ACI rats were heterotypically transplanted into Lewis rat abdomens in end-to-end fashion with minimal ischemic time. 55 rats were assigned to five groups as follows:

0 mg/kg/d Compound A(vehicle)(N=10);

10 mg/kg/d Compound A (N=10);

20 mg/kg/d Compound A (N=10), 40 mg/kg/d Compound A (N=10), cyclosporin 10 mg/kg/d, PO (N=10); and isograft negative control (Lewis-to-Lewis, N=5).

Compound A was administered subcutaneously to recipient animals three days prior to the surgery and once daily for 90 days thereafter. Due to failure to gain weight and skin irritation, the group receiving 40 mg/kg/d received this dose for only 13 days. Thereafter, the dose was reduced to 30 mg/kg/d for 6 days and then further reduced to 5 mg/kg/d for the remainder of the study.

On day 90, the allograft segment was removed, fixed in 10% buffered formalin and paraffin embedded. Sections were stained with von Geisson's elastic stain, and intima-to-media area (IM) ratio and percent luminal narrowing (% LN) were assessed by digital morphometry (See FIGS. 1 and 2). Blood was collected at regular intervals throughout the study and plasma evaluated for compound levels (See FIG. 3).

The treatment with Compound A was well tolerated at the 10, and 20 mg/kg/d doses and animals regained weight post surgery. The group treated with the 40 mg/kg/d initially lost weight until the dose was dropped to 5 mg/kg/d after which time they gained weight similar to vehicle controls. Recipient animals treated with Compound A had significantly lower IM ratio and % LN when compared to the vehicle group at the 20 mg and 40/30/5 mg/kg/d doses. The group receiving the 40/30/5 mg/kg/d dose of Compound A evidenced the highest degree of inhibition despite the fact that it received only a 40 mg/kg/d dose for 13 days prior to dosing down. The percent inhibition of IM ratio in Compound A treated animals were 11%, 28% and 49%, at the 10, 20 and 40/30/5 doses respectively when compared to vehicle control animals. The percent inhibition of the % LN was 22%, 33% and 52% at the 10, 20 and 40/30/5 treated animals when compared to vehicle control animals. Cyclosporin (CsA) inhibited IM and % LN by 98% and 94% compared with vehicle control. After 90 days of dosing, the trough plasma levels were 10, 18 and 28 μM for the 10, 20 and 40/30/5 mg/kg/d doses, respectively.

Compound A evidenced dose-dependent inhibition of aortic neointimal growth, a feature of graft arteriosclerosis associated with chronic transplantation rejection. At the 20 mg/kg/d dose it was efficacious without grossly discernable toxic side effects. The 40/30/5 mg/kg/d dose given for 14 days resulted in the greatest degree of inhibition suggesting that an initial high dose of compound may provide long term beneficial effects.

We claim:

1. A method for treating transplant rejection in a mammal comprising administering to said mammal an effective amount of a compound of formula

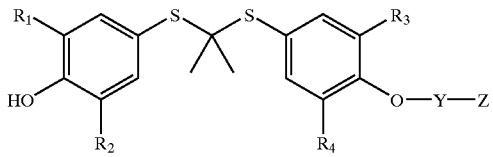

or a pharmaceutically acceptable salt thereof wherein:
Y is a bond or

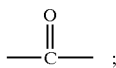

$R_1$, $R_2$, $R_3$, and $R_4$ are independently selected from the group consisting of hydrogen, hydroxy, $C_{1-10}$alkyl, aryl, heteroaryl, $C_{1-10}$alkaryl, and aryl $C_{1-10}$alkyl, wherein all nonhydrogen and hydroxy substituents may optionally be substituted from one or more of the group selected from $C_{1-10}$alkyl, halogen, nitro, amino, halo$_{1-10}$alkyl, $C_{1-10}$alkylamino, di$C_{1-10}$alkylamino, acyl, and acyloxy;

Z is selected from the group consisting of $C_{1-10}$alkyl, $C_{2-10}$alkenyl, $C_{2-10}$alkynyl, hydroxy$C_{1-10}$alkyl, aryl, heteroaryl, $C_{1-10}$alkaryl, aryl$C_{1-10}$alkyl, heteroaryl-$C_{1-10}$alkyl, $C_{1-10}$alkoxy$C_{1-10}$alkyl, $C_{1-10}$alkylamino-$C_{1-10}$alkyl, carboxy$C_{1-10}$alkyl, $C_{1-10}$dialkylamino-$C_{1-10}$alkyl, amino$C_{1-10}$alkyl, heterocycle, heterocycl$C_{1-10}$alkyl, $R_7$NH, $R_7R_7$N, carboxy, carbohydrate group, carbohydrate lactone group, and an alditol group wherein all may optionally be substituted by one or more $R_5$;

$R_5$ is independently selected from the group selected from hydroxy, $C_{1-10}$alkyl, $C_{1-10}$alkoxy, halo, nitro, amino, cyano, $C_{1-10}$alkylamino, di$C_{1-10}$alkylamino, acyl, acyloxy, COOH, COOR$_7$, OC(O)R$_7$, CH(OH)R$_7$, NHR$_7$, NR$_7$R$_7$, C(O)NH$_2$, C(O)NHR$_7$, CONR$_7$R$_7$, NHC(O)O—R$_7$, OSO$_3$H, SO$_3$H, SO$_2$NHR$_7$, SO$_2$NR$_7$R$_7$, P(O)(OH)OR$_7$, PO$_2$H$_2$P(O)(OH)R$_7$, P(O)(OR$_7$)$_2$, P(O)R$_7$(OR$_7$), OPO$_3$H, PO$_3$H$_2$, hydroxymethyl, and cyclic phosphate, wherein when possible, all may be optionally substituted by one or more $R_6$;

$R_6$ is independently selected from the group consisting of hydroxy, $C_{1-10}$alkyl, $C_{1-10}$alkoxy, acyloxy, halo, nitro, amino, cyano, halo$C_{1-10}$alkyl, $C_{1-10}$alkylamino, di$C_{1-10}$alkylamino, acyl, and acyloxy;

$R_7$ is independently selected from the group consisting of $C_{1-10}$alkyl, $C_{2-10}$alkenyl, $C_{2-10}$alkynyl, $C_{1-10}$alkoxy, $C_{1-10}$alkoxycarbonyl$C_{1-10}$alkyl, aryl, carboxy-$C_{1-10}$alkyl, $C_{1-10}$alkylcarboxy$C_{1-10}$alkyl, $C_{1-10}$alkylcarboxy$C_{1-10}$aryl, heterocycle, heterocycl-$C_{1-10}$alkyl, and heteroaryl, wherein all may be optionally substituted by one or more $R_8$; and $R_8$ is independently selected from the group consisting of hydroxy, $C_{1-10}$alkyl, $C_{1-10}$alkoxy, acyloxy, halo, nitro, amino, cyano, and carboxy;

wherein two $R_7$ groups may come together to form a 4 to 7 membered ring.

2. A method for treating transplant rejection in a mammal comprising administering to said mammal an effective amount of a compound of formula

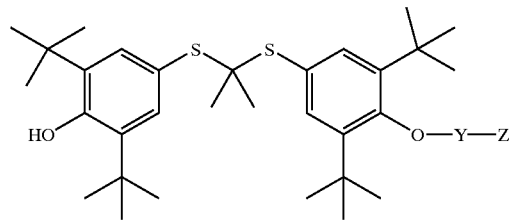

or a pharmaceutically acceptable salt wherein:
Y is a bond;
Z is selected from the group consisting of $C_{1-10}$alkyl, $C_{2-10}$alkenyl, $C_{2-10}$alkynyl, hydroxy$C_{1-10}$alkyl, aryl, heteroaryl, $C_{1-10}$alkaryl, aryl$C_{1-10}$alkyl, heteroaryl-$C_{1-10}$alkyl, $C_{1-10}$alkoxy$C_{1-10}$alkyl, $C_{1-10}$alkylamino-$C_{1-10}$alkyl, carboxy$C_{1-10}$alkyl, $C_{1-10}$dialkylamino-$C_{1-10}$alkyl, amino$C_{1-10}$alkyl, heterocycle, heterocycl$C_{1-10}$alkyl, $R_7$NH, $R_7R_7$N, carbohydrate group, carbohydrate lactone group, and an alditol group wherein all may optionally be substituted by one or more $R_5$;

$R_5$ is independently selected from the group selected from hydroxy, $C_{1-10}$alkyl, $C_{1-10}$alkoxy, halo, nitro, amino, cyano, $C_{1-10}$alkylamino, di$C_{1-10}$alkylamino, acyl, acyloxy, COOH, COOR$_7$, OC(O)R$_7$, CH(OH)R$_7$, NHR$_7$, NR$_7$R$_7$, C(O)NH$_2$, C(O)NHR$_7$, CONR$_7$R$_7$, NHC(O)O—R$_7$, OSO$_3$H, SO$_3$H, SO$_2$NHR$_7$, SO$_2$NR$_7$R$_7$, P(O)(OH)OR$_7$, PO$_2$H$_2$ P(O)(OH)R$_7$, P(O)(OR$_7$)$_2$, P(O)R$_7$(OR$_7$), OPO$_3$H, PO$_3$H$_2$, hydroxymethyl, and cyclic phosphate, wherein when possible, all may be optionally substituted by one or more $R_6$;

$R_6$ is independently selected from the group consisting of hydroxy, $C_{1-10}$alkyl, $C_{1-10}$alkoxy, acyloxy, halo, nitro, amino, cyano, halo$C_{1-10}$alkyl, $C_{1-10}$alkylamino, di$C_{1-10}$alkylamino, acyl, and acyloxy;

$R_7$ is independently selected from the group consisting of $C_{1-10}$alkyl, $C_{2-10}$alkenyl, $C_{2-10}$alkynyl, $C_{1-10}$alkoxy, C$_{1-10}$alkoxycarbonylC$_{1-10}$alkyl, aryl, carboxy-C$_{1-10}$alkyl, C$_{1-10}$alkylcarboxyC$_{1-10}$alkyl, C$_{1-10}$alkylcarboxyC$_{1-10}$aryl, heterocycle, heterocycl-C$_{1-10}$alkyl, and heteroaryl, wherein all may be optionally substituted by one or more R$_8$; and R$_8$ is independently selected from the group consisting of hydroxy, C$_{1-10}$alkyl, C$_{1-10}$alkoxy, acyloxy, halo, nitro, amino, cyano, and carboxy;

wherein two R$_7$ groups may come together to form a 4 to 7 membered ring.

3. The method of claim 2, wherein:

Z is selected from the group consisting of C$_{1-6}$alkyl, hydroxyC$_{1-6}$alkyl, C$_{1-6}$alkoxyC$_{1-6}$alkyl, and carboxyC$_{1-6}$alkyl, wherein all may optionally be substituted by one or more R$_5$;

R$_5$ is independently selected from the group selected from hydroxy, amino, halo, COOH, COOR$_7$, CH(OH)R$_7$, NHR$_7$, NR$_7$R$_7$, C(O)NH$_2$, C(O)NHR$_7$, CONR$_7$R$_7$, OSO$_3$H, SO$_3$H, SO$_2$NHR$_7$, SO$_2$NR$_7$R$_7$, P(O)(OH)OR$_7$, P(O)(OH)R$_7$, P(O)HR$_7$, P(OR$_7$)$_2$, P(O)R$_7$(OR$_7$), OPO$_3$H, PO$_3$H$_2$, and hydroxymethyl, wherein when possible, all may be optionally substituted by one or more R$_6$;

R$_6$ is independently selected from the group consisting of hydroxy, C$_{1-10}$alkyl, C$_{1-10}$alkoxy, acyloxy, halo, nitro, amino, cyano, haloC$_{1-10}$alkyl, C$_{1-10}$alkylamino, di-C$_{1-10}$alkylamino, acyl, and acyloxy;

R$_7$ is independently selected from the group consisting of C$_{1-6}$alkyl, C$_{2-10}$alkenyl, C$_{2-6}$alkynyl, C$_{1-6}$alkoxy, C$_{1-6}$alkoxycarbonylC$_{1-6}$alkyl, carboxyC$_{1-6}$alkyl, and C$_{1-6}$alkylcarboxyC$_{1-6}$alkyl, wherein all may be optionally substituted by one or more R$_8$; and R$_8$ is independently selected from the group consisting of hydroxy, C$_{1-6}$alkyl, C$_{1-6}$alkoxy, acyloxy, halo, amino, cyano, and carboxy.

4. The method of claim 3, wherein:

Z is C$_{1-6}$alkyl, optionally substituted by one or more R$_5$;

R$_5$ is independently selected from the group consisting of halo, COOH, COOR$_7$, CONH$_2$, CONHR$_7$, CONR$_7$R$_7$, and amino;

R$_7$ is independently selected from the group consisting of C$_{1-6}$alkyl, carboxyC$_{1-6}$alkyl, C$_{1-6}$alkoxycarbonylC$_{1-6}$alkyl, and C$_{1-6}$alkylcarboxyC$_{1-6}$alkyl, wherein all may be optionally substituted by one or more R$_8$; and R$_8$ is independently selected from the group consisting of hydroxy, halo, amino, and carboxy.

5. The method of claim 4, wherein:

Z is C$_{1-6}$alkyl, optionally substituted by one or more R$_5$; and

R$_5$ is COOH.

6. The method of claim 5, wherein the compound or its pharmaceutically acceptable salt is selected from the group consisting of

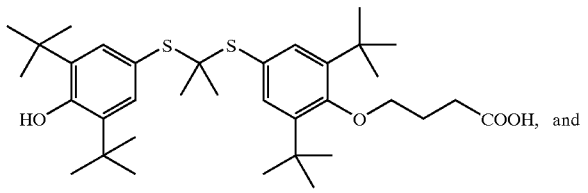

-continued

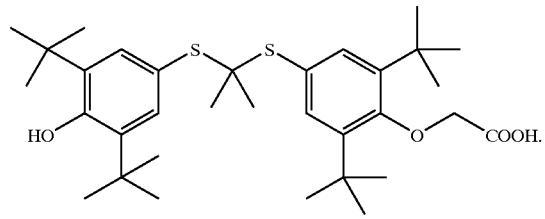

7. The method of claim 6, wherein the compound or its pharmaceutically acceptable salt is

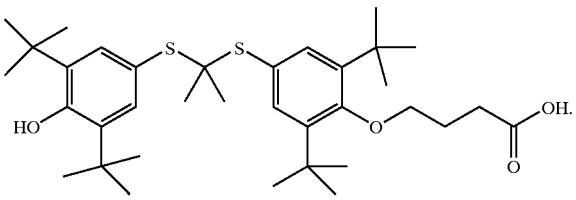

8. The method of claim 2, wherein:

Z is an alditol, optionally substituted with one or more R$_5$; and

R$_5$ is independently selected from the group consisting of halo, amino, carboxy, diC$_{1-6}$alkylamino, and C$_{1-6}$alkylamino.

9. The method of claim 8, wherein the compound or its pharmaceutically acceptable salt is selected from the group consisting of

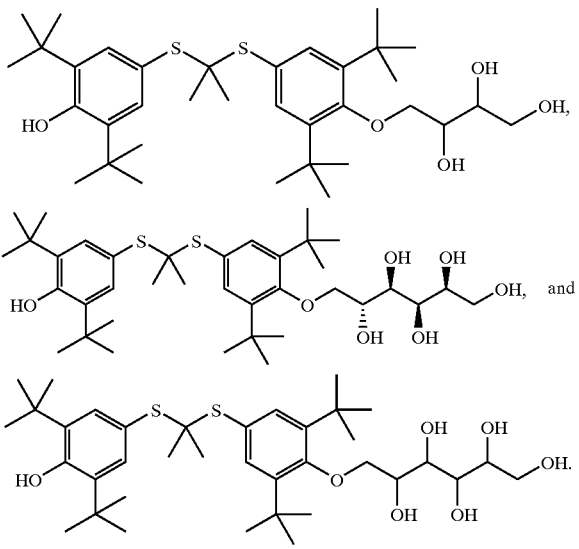

10. The method of claim 2, wherein:

Z is a carbohydrate or a carbohydrate lactone, optionally substituted by one or more R$_5$; and R$_5$ is independently selected from the group consisting of halo, amino, carboxy, diC$_{1-6}$alkylamino, acyloxy, and C$_{1-6}$alkylamino.

11. The method of claim 10, wherein the compound or its pharmaceutically acceptable salt is selected form the group consisting of

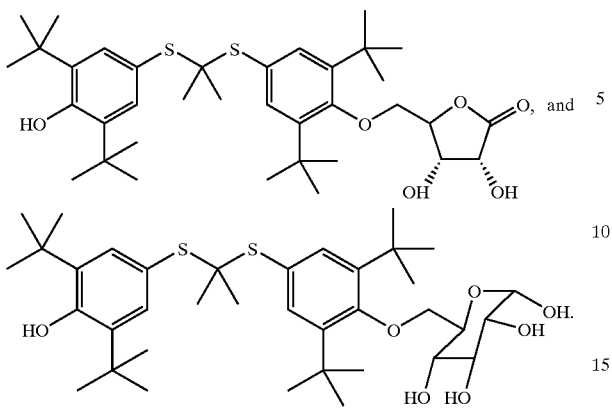

12. The method of claim 2, wherein:

Z is selected from the group consisting of $C_{1-6}$alkyl, $C_{1-6}$alkoxy$C_{1-6}$alkyl, $C_{1-6}$alkylamino$C_{1-6}$alkyl, $C_{1-6}$dialkylamino$C_{1-6}$alkyl, and amino$C_{1-6}$alkyl, wherein all may optionally be substituted by one or more $R_5$;

$R_5$ is independently selected from the group selected from hydroxy, $C_{1-6}$alkyl, $C_{1-6}$alkoxy, acyloxy, halo, nitro, amino, cyano, $C_{1-6}$alkylamino, di$C_{1-6}$alkylamino, acyl, acyloxy, COOH, COOR$_7$, OC(O)R$_7$, CH(OH)R$_7$, NHR$_7$, NR$_7$R$_7$, C(O)NH$_2$, C(O)NHR$_7$, CONR$_7$R$_7$, NHC(O)O—R$_7$, OSO$_3$H, SO$_3$H, SO$_2$NHR$_7$, SO$_2$NR$_7$R$_7$, P(O)(OH)OR$_7$, P(O)HR$_7$, P(O)(OH)R$_7$)$_2$, P(O)R$_7$(OR$_7$), OPO$_3$H, PO$_3$H$_2$, hydroxymethyl, and cyclic phosphate, wherein when possible, all may be optionally substituted by one or more $R_6$;

$R_6$ is independently selected from the group consisting of hydroxy, $C_{1-6}$alkyl, $C_{1-6}$alkoxy, acyloxy, halo, amino, cyano, halo$C_{1-6}$alkyl, $C_{1-6}$alkylamino, di$C_{1-6}$alkylamino, acyl, and acyloxy;

$R_7$ is independently selected from the group consisting of $C_{1-6}$alkyl, $C_{2-10}$loalkenyl, $C_{2-10}$alkynyl, $C_{1-10}$alkoxy, $C_{1-10}$alkoxycarbonyl$C_{1-10}$alkyl, carboxy$C_{1-6}$alkyl, $C_{1-6}$alkylcarboxy$C_{1-6}$alkyl, and heteroaryl, wherein all may be optionally substituted by one or more $R_8$; and $R_8$ is independently selected from the group consisting of hydroxy, halo, amino, and carboxy.

13. The method of claim 12, wherein the compound or its pharmaceutically acceptable salt is selected form the group consisting of

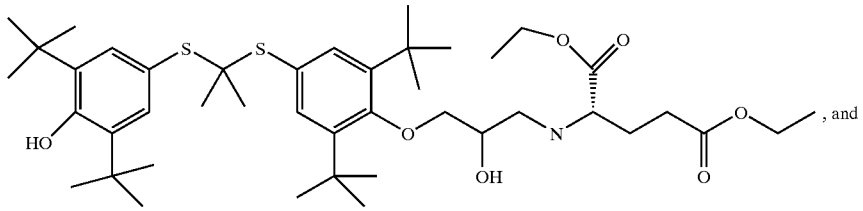

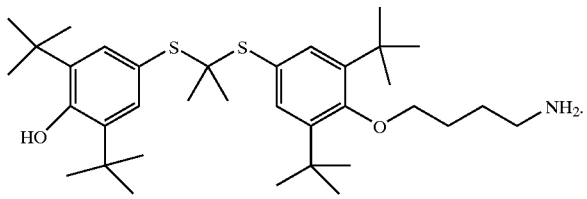

14. The method of claim 2, wherein:

Z is selected from the group consisting of $C_{1-6}$alkyl, aryl, heteroaryl, $C_{1-6}$alkaryl, aryl$C_{1-6}$alkyl, heteroaryl$C_{1-6}$alkyl, heterocycle, and heterocycl$C_{1-6}$alkyl, wherein all may optionally be substituted by one or more $R_5$;

$R_5$ is independently selected from the group selected from hydroxy, $C_{1-6}$alkyl, $C_{1-6}$alkoxy, acyloxy, halo, nitro, amino, cyano, $C_{1-6}$alkylamino, di$C_{1-6}$alkylamino, acyl, acyloxy, COOH, COOR$_7$, OC(O)R$_7$, CH(OH)R$_7$, NHR$_7$, NR$_7$R$_7$, C(O)NH$_2$, C(O)NHR$_7$, CONR$_7$R$_7$, NHC(O)O—R$_7$, OSO$_3$H, SO$_3$H, SO$_2$NHR$_7$, SO$_2$NR$_7$R$_7$, P(O)(OH)OR$_7$, P(O)HR$_7$, P(O)(OH)R$_7$)$_2$, P(O)R$_7$(OR$_7$), OPO$_3$H, PO$_3$H$_2$, hydroxymethyl, and cyclic phosphate, wherein when possible, all may be optionally substituted by one or more $R_6$;

$R_6$ is independently selected from the group consisting of hydroxy, $C_{1-6}$alkyl, $C_{1-6}$alkoxy, acyloxy, halo, amino, cyano, halo$C_{1-6}$alkyl, $C_{1-6}$alkylamino, di$C_{1-6}$alkylamino, acyl, and acyloxy;

R<sub>7</sub> is independently selected from the group consisting of C$_{1-6}$alkyl, C$_{2-10}$alkenyl, C$_{2-10}$alkynyl, C$_{1-10}$alkoxy, C$_{1-10}$alkoxycarbonylC$_{1-10}$alkyl, aryl, carboxyC$_{1-6}$alkyl, C$_{1-6}$alkylcarboxyC$_{1-6}$alkyl, C$_{1-6}$alkylcarboxyC$_{1-6}$aryl, heterocycle, heterocyclC$_{1-6}$alkyl, and heteroaryl, wherein all may be optionally substituted by one or more R$_8$; and R$_8$ is independently selected from the group consisting of hydroxy, halo, amino, and carboxy; wherein two R$_7$ groups may come together to form a 4 to 7 membered ring.

15. A method for treating transplant rejection in a mammal comprising administering to said mammal an effective amount of a compound of formula

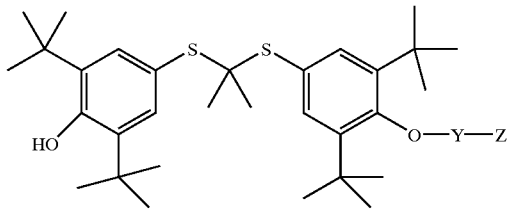

or a pharmaceutically acceptable salt wherein:

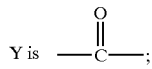

Y is

Z is selected from the group consisting of C$_{1-10}$alkyl, C$_{2-10}$alkenyl, C$_{2-10}$alkynyl, hydroxyC$_{1-10}$alkyl, aryl, heteroaryl, C$_{1-10}$alkaryl, aryl$_{1-10}$alkyl, heteroaryl-C$_{1-10}$alkyl, C$_{1-10}$alkoxyC$_{1-10}$alkyl, C$_{1-10}$alkylamino-C$_{1-10}$alkyl, carboxyC$_{1-10}$alkyl, C$_{1-10}$dialkylamino-C$_{1-10}$alkyl, aminoC$_{1-10}$alkyl, heterocycle, heterocyclC$_{1-10}$alkyl, R$_7$NH, R$_7$R$_7$N, carboxy, carbohydrate group, carbohydrate lactone group, and an alditol group wherein all may optionally be substituted by one or more R$_5$;

R$_5$ is independently selected from the group selected from hydroxy, C$_{1-10}$alkyl, C$_{1-10}$alkoxy, halo, nitro, amino, cyano, C$_{1-10}$alkylamino, diC$_{1-10}$alkylamino, acyl, acyloxy, COOH, COOR$_7$, OC(O)R$_7$, CH(OH)R$_7$, NHR$_7$, NR$_7$R$_7$, C(O)NH$_2$, C(O)NHR$_7$, CONR$_7$R$_7$, NHC(O)O—R$_7$, OSO$_3$H, SO$_3$H, SO$_2$NHR$_7$, SO$_2$NR$_7$R$_7$, P(O)(OH)OR$_7$, PO$_2$H$_2$P(O)(OH)R$_7$, P(O)(OR$_7$)$_2$, P(O)R$_7$(OR$_7$), OPO$_3$H, PO$_3$H$_2$, hydroxymethyl, and cyclic phosphate, wherein when possible, all may be optionally substituted by one or more R$_6$;

R$_6$ is independently selected from the group consisting of hydroxy, C$_{1-10}$alkyl, C$_{1-10}$alkoxy, acyloxy, halo, nitro, amino, cyano, haloC$_{1-10}$alkyl, C$_{1-10}$alkylamino, diC$_{1-10}$alkylamino, acyl, and acyloxy;

R$_7$ is independently selected from the group consisting of C$_{1-10}$alkyl, C$_{2-10}$alkenyl, C$_{2-10}$alkynyl, C$_{1-10}$alkoxy, C$_{1-10}$alkoxycarbonylC$_{1-10}$alkyl, aryl, carboxyC$_{1-10}$alkyl, C$_{1-10}$alkylcarboxyC$_{1-10}$alkyl, C$_{1-10}$alkylcarboxyC$_{1-10}$aryl, heterocycle, heterocyclC$_{1-10}$alkyl, and heteroaryl, wherein all may be optionally substituted by one or more R$_8$; and R$_8$ is independently selected from the group consisting of hydroxy, C$_{1-10}$alkyl, C$_{1-10}$alkoxy, acyloxy, halo, nitro, amino, cyano, and carboxy;

wherein two R$_7$ groups may come together to form a 4 to 7 membered ring.

16. The method of claim 15, wherein:

Z is selected from the group consisting of C$_{1-6}$alkyl, hydroxyC$_{1-6}$alkyl, C$_{1-6}$alkoxyC$_{1-6}$alkyl, and carboxyC$_{1-6}$alkyl, wherein all may optionally be substituted by one or more R$_5$;

R$_5$ is independently selected from the group selected from hydroxy, amino, halo, COOH, COOR$_7$, CH(OH)R$_7$, NHR$_7$, NR$_7$R$_7$, C(O)NH$_2$, C(O)NHR$_7$, CONR$_7$R$_7$, OSO$_3$H, SO$_3$H, SO$_2$NHR$_7$, SO$_2$NR$_7$R$_7$, P(O)(OH)OR$_7$, P(O)(OH)R$_7$, P(O)HR$_7$, P(OR$_7$)$_2$, P(O)R$_7$(OR$_7$), OPO$_3$H, PO$_3$H$_2$, and hydroxymethyl, wherein when possible, all may be optionally substituted by one or more R$_6$;

R$_7$ is independently selected from the group consisting of C$_{1-6}$alkyl, C$_{2-10}$alkenyl, C$_{2-6}$alkynyl, C$_{1-6}$alkoxy, C$_{1-6}$alkoxycarbonylC$_{1-6}$alkyl, carboxyC$_{1-6}$alkyl, and C$_{1-6}$alkylcarboxyC$_{1-6}$alkyl, wherein all may be optionally substituted by one or more R$_8$; and R$_8$ is independently selected from the group consisting of hydroxy, C$_{1-6}$alkyl, C$_{1-6}$alkoxy, acyloxy, halo, amino, cyano, and carboxy.

17. The method of claim 16, wherein:

Z is C$_{1-6}$alkyl, optionally substituted by one or more R$_5$;

R$_5$ is independently selected from the group consisting of halo, COOH, COOR$_7$, CONH$_2$, CONHR$_7$, CONR$_7$R$_7$, and amino;

R$_7$ is independently selected from the group consisting of C$_{1-6}$alkyl, carboxyC$_{1-6}$alkyl, and C$_{1-6}$alkylcarboxyC$_{1-6}$alkyl, wherein all may be optionally substituted by one or more R$_8$; and R$_8$ is independently selected from the group consisting of hydroxy, halo, amino, and carboxy.

18. The method of claim 17, wherein:

Z is C$_{1-6}$alkyl, optionally substituted by one or more R$_5$; and

R$_5$ is COOH.

19. The method of claim 18, wherein the compound or its pharmaceutically acceptable salt is selected from the group consisting of

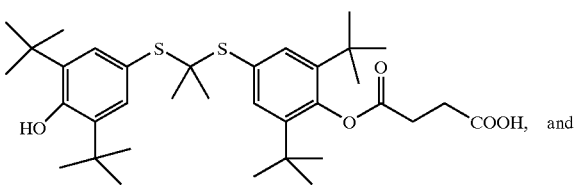

, and

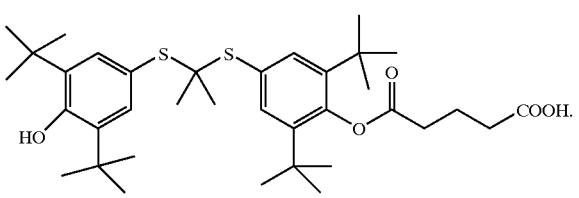

.

20. The method of claim 19, wherein the compound or its pharmaceutically acceptable salt is

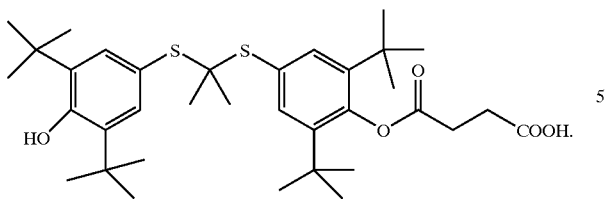

21. The method of claim 15, wherein:

Z is selected from the group consisting of $C_{1-6}$alkyl, $C_{1-6}$alkoxy$C_{1-6}$alkyl, $C_{1-6}$alkylamino$C_{1-6}$alkyl, and amino$C_{1-6}$alkyl, wherein all may optionally be substituted by one or more $R_5$;

$R_5$ is independently selected from the group selected from hydroxy, $C_{1-6}$alkyl, $C_{1-6}$alkoxy, acyloxy, halo, nitro, amino, cyano, $C_{1-6}$alkylamino, di$C_{1-6}$alkylamino, acyl, acyloxy, COOH, COOR$_7$, OC(O)R$_7$, CH(OH)R$_7$, NHR$_7$, NR$_7$R$_7$, C(O)NH$_2$, C(O)NHR$_7$, CONR$_7$R$_7$, NHC(O)O—R$_7$, OSO$_3$H, SO$_3$H, SO$_2$NHR$_7$, SO$_2$NR$_7$R$_7$, P(O)(OH)OR$_7$, P(O)HR$_7$, P(O)(OH)R$_7$, P(OR$_7$)$_2$, P(O)R$_7$(OR$_7$), OPO$_3$H, PO$_3$H$_2$, hydroxymethyl, and cyclic phosphate, wherein when possible, all may be optionally substituted by one or more $R_6$;

$R_6$ is independently selected from the group consisting of hydroxy, $C_{1-6}$alkyl, $C_{1-6}$alkoxy, acyloxy, halo, amino, cyano, halo$C_{1-6}$alkyl, $C_{1-6}$alkylamino, di$C_{1-6}$alkylamino, acyl, and acyloxy;

$R_7$ is independently selected from the group consisting of $C_{1-6}$alkyl, $C_{2-10}$loalkenyl, $C_{2-10}$alkynyl, $C_{1-10}$alkoxy, $C_{1-10}$alkoxycarbonyl$C_{1-10}$alkyl, carboxy$C_{1-6}$alkyl, $C_{1-6}$alkylcarboxy$C_{1-6}$alkyl, and heteroaryl, wherein all may be optionally substituted by one or more $R_8$; and $R_8$ is independently selected from the group consisting of hydroxy, halo, amino, and carboxy.

22. The method of claim 21, wherein the compound or its pharmaceutically acceptable salt is

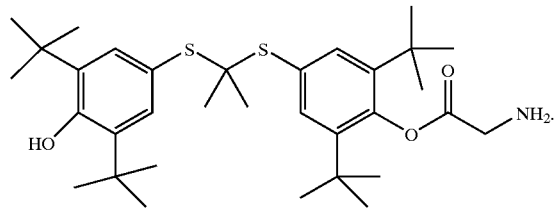

23. The method of claim 15, wherein:

Z is selected from the group consisting of $C_{1-6}$alkyl, aryl, heteroaryl, $C_{1-6}$alkaryl, aryl$C_{1-6}$alkyl, heteroaryl$C_{1-6}$alkyl, heterocycle, and heterocyclC$_{1-6}$alkyl, wherein all may optionally be substituted by one or more $R_5$;

$R_5$ is independently selected from the group selected from hydroxy, $C_{1-6}$alkyl, $C_{1-6}$alkoxy, acyloxy, halo, nitro, amino, cyano, $C_{1-6}$alkylamino, di$C_{1-6}$alkylamino, acyl, acyloxy, COOH, COOR$_7$, OC(O)R$_7$, CH(OH)R$_7$, NHR$_7$, NR$_7$R$_7$, C(O)NH$_2$, C(O)NHR$_7$, CONR$_7$R$_7$, NHC(O)O—R$_7$, OSO$_3$H, SO$_3$H, SO$_2$NHR$_7$, SO$_2$NR$_7$R$_7$, P(O)(OH)OR$_7$, P(O)HR$_7$, P(O)(OH)R$_7$, P(OR$_7$)$_2$, P(O)R$_7$(OR$_7$), OPO$_3$H, PO$_3$H$_2$, hydroxymethyl, and cyclic phosphate, wherein when possible, all may be optionally substituted by one or more $R_6$;

$R_6$ is independently selected from the group consisting of hydroxy, $C_{1-6}$alkyl, $C_{1-6}$alkoxy, acyloxy, halo, amino, cyano, halo$C_{1-6}$alkyl, $C_{1-6}$alkylamino, di$C_{1-6}$alkylamino, acyl, and acyloxy;

$R_7$ is independently selected from the group consisting of $C_{1-6}$alkyl, $C_{2-10}$alkenyl, $C_{2-10}$alkynyl, $C_{1-10}$alkoxy, $C_{1-10}$alkoxycarbonyl$C_{1-10}$alkyl, aryl, carboxy$C_{1-6}$alkyl, $C_{1-6}$alkylcarboxy$C_{1-6}$alkyl, $C_{1-6}$alkylcarboxy-$C_{1-6}$aryl, heterocycle, heterocyclC$_{1-6}$alkyl, and heteroaryl, wherein all may be optionally substituted by one or more $R_8$; and $R_8$ is independently selected from the group consisting of hydroxy, halo, amino, and carboxy;

wherein two $R_7$ groups may come together to form a 4 to 7 membered ring.

24. A method for treating transplant rejection in a mammal comprising administering to said mammal in combination a compound of claim 1, claim 2, or claim 15 and one or more compound selected from the group consisting of cyclosporin, tacrolimus (FK506), sirolimus (rapamycin), methotrexate, mycophenolic acid (mycophenolate mofetil), everolimus, azathiprine, steroids and NOX-100, said combination being administered in an amount effective to inhibit or modulate transplant rejection.

25. A compound of the formula

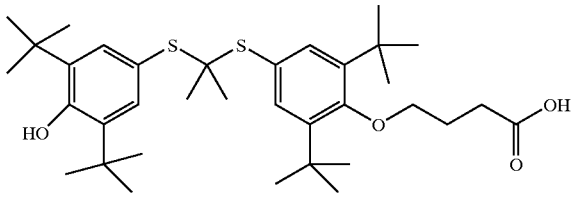

or its pharmaceutically acceptable salt thereof.

* * * * *